(12) United States Patent
Chiang

(10) Patent No.: US 6,620,830 B2
(45) Date of Patent: Sep. 16, 2003

(54) THYROID RECEPTOR LIGANDS

(75) Inventor: Yuan-Ching P. Chiang, East Lyme, CT (US)

(73) Assignee: Pfizer, Inc., New York, NY (US)

( * ) Notice: Subject to any disclaimer, the term of this patent is extended or adjusted under 35 U.S.C. 154(b) by 0 days.

(21) Appl. No.: 09/836,765

(22) Filed: Apr. 17, 2001

(65) Prior Publication Data

US 2001/0051645 A1 Dec. 13, 2001

Related U.S. Application Data

(60) Provisional application No. 60/199,044, filed on Apr. 21, 2000.

(51) Int. Cl.[7] .................... C07D 277/34; A61K 31/425
(52) U.S. Cl. ........................... 514/369; 548/183
(58) Field of Search .................... 548/183; 514/369

(56) References Cited

U.S. PATENT DOCUMENTS

| | | | |
|---|---|---|---|
| 4,069,343 A | 1/1978 | Sellstedt et al. | 434/319 |
| 4,554,290 A | 11/1985 | Boger et al. | 514/487 |
| 4,766,121 A | 8/1988 | Ellis et al. | 514/247 |
| 4,826,876 A | 5/1989 | Ellis et al. | 514/535 |
| 4,910,305 A | 3/1990 | Ellis et al. | 544/239 |
| 5,061,798 A | 10/1991 | Emmett et al. | 544/239 |
| 5,232,947 A | 8/1993 | Sato et al. | 514/549 |
| 5,284,971 A | 2/1994 | Walker et al. | 562/429 |
| 5,401,772 A | 3/1995 | Yokoyama et al. | 514/539 |
| 5,569,674 A | 10/1996 | Yokoyama et al. | 514/539 |
| 5,654,468 A | 8/1997 | Yokoyama et al. | 560/43 |

FOREIGN PATENT DOCUMENTS

| | | | |
|---|---|---|---|
| EP | 0580550 | 10/1997 | C07C/233/56 |
| JP | 31660 | 6/2001 | C07D/277/34 |
| WO | WO9924415 | 5/1999 | C07D/277/34 |

OTHER PUBLICATIONS

Ebisawa, M. et al., Chem. Pharm. Bull., 47(9) 1348–1350 (1999), "Thiazolidinediones With Thyroid Hormone Receptor Antagonistic Activity".

Ebisawa, M. et al., Biol. Pharm. Bull., 21(5), 547–549(1998), "Novel Thiazolidinedione Derivatives With Retinoid Synergistic Activity".

Yokoyama, N. et al., J. Med. Chem. 1995, 38, 695–707, "Synthesis and Structure—Activity Relationships of Oxamic Acid and Acetic Acid Derivatives Related to $_L$–Thyronine".

Stephan, Z. F. et al., Atherosclerosis 126 (1996) 53–63, "Demonstration of Potent Lipid–Lowering Activity by a Thyromimetic Agent Devoid of Cardiovascular and Thermogenic Effects".

Steele, R. E. et al., Atherosclerosis X, (1995), pp. 321–324, "CGS 26214, The Thyroxine Connection Revisited".

*Primary Examiner*—Robert Gerstl

(57) ABSTRACT

The invention provides thiazolidinedione, oxadiazolidinedione, and triazolone compounds of Formula (I) which compounds are thyroid receptor ligands.

(I)

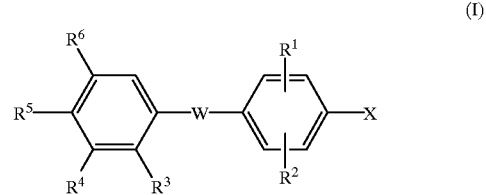

The invention further provides pharmaceutical compositions and kits comprising such compounds and methods of treating obesity, overweight condition, hyperlipidemia, glaucoma, cardiac arrhythmias, skin disorders, thyroid disease, hypothyroidism, thyroid cancer, diabetes, atherosclerosis, hypertension, coronary heart disease, congestive heart failure, hypercholesterolemia, depression, and osteoporosis using such compounds.

18 Claims, No Drawings

THYROID RECEPTOR LIGANDS

CROSS REFERENCE TO RELATED APPLICATION

This application claims priority of U.S. provisional application No. 60/199,044, filed Apr. 21, 2000.

FIELD OF THE INVENTION

The present invention relates to certain thiazolidinedione, oxadiazolidinedione, and triazolone compounds which are thyroid receptor ligands.

The invention further relates to pharmaceutical compositions and kits comprising such thiazolidinedione, oxadiazolidinedione, and triazolone compounds and to methods of using such compounds in the treatment of obesity, overweight condition, hyperlipidemia, glaucoma, cardiac arrhythmias, skin disorders, thyroid disease, hypothyroidism, thyroid cancer, diabetes, atherosclerosis, hypertension, coronary heart disease, congestive heart failure, hypercholesterolemia, depression, and osteoporosis.

BACKGROUND OF THE INVENTION

Thyroid hormones are critical for normal development and for the maintenance of metabolic homeostasis. As such, thyroid hormones are known to stimulate the metabolism of cholesterol to bile acids and enhance the lipolytic responses of fat cells to other hormones.

Thyroid hormones further affect cardiac function both directly and indirectly, e.g., by increasing the metabolic rate. For example, tachycardia, increased stroke volume, increased cardiac index, cardiac hypertrophy, decreased peripheral vascular resistance and increased pulse pressure are all observed in patients with hyperthyroidism.

Disorders of the thyroid gland resulting in decreased levels of thyroid hormones are normally treated by administering either naturally occurring thyroid hormones or analogues thereof that mimic the effects of thyroid hormones. Such analogues are known generically as thyromimetics or thyroid receptor ligands.

Two naturally occurring thyroid hormones, 3,5,3'-triiodo-L-thyronine (also referred to as "$T_3$"), and 3,5,3',5'-tetraiodo-L-thyronine (also referred to as "$T_4$" or thyroxine), are depicted hereinbelow:

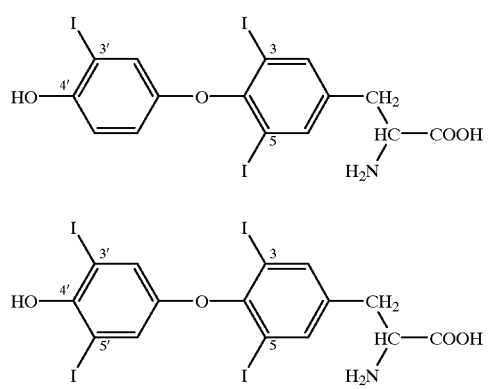

Generally, $T_3$ is more biologically active than $T_4$, and differs therefrom by the absence of an iodine atom in the 5' position. $T_3$ may be produced directly, in either the thyroid gland or in peripheral tissues, by removal of the 5' iodine of $T_4$ by deiodinase enzymes. Synthetic thyroid receptor ligands can be designed to be structurally similar to $T_3$. In addition, naturally occurring metabolites of $T_3$ are known.

As discussed hereinabove, thyroid hormones may affect cardiac functioning, for example, by causing an increase in heart rate and, accordingly, an increase in oxygen consumption. While the increase in oxygen consumption can result in certain desirable metabolic effects, such increase places additional burden on the heart which, in many situations, results in detrimental side effects. Consequently, efforts have been made to synthesize thyroid hormone analogs/mimetics that function to lower lipids and serum cholesterol, but which have reduced adverse cardiac effects.

A variety of thyroid hormone analogs/mimetics are described and referenced hereinbelow, however, additional agents will be known to one of ordinary skill in the art. For example, U.S. Pat. Nos. 4,766,121; 4,826,876; 4,910,305; and 5,061,798 disclose thyroid hormone mimetics, namely, 3,5-dibromo-3'-[6-oxo-3(1H)-pyridazinylmethyl]-thyronines, while U.S. Pat. No. 5,284,971 discloses thyromimetic cholesterol lowering agents, namely, 4-(3-cyclohexyl-4-hydroxy or -methoxy phenylsulfonyl)-3,5 dibromo-phenylacetic compounds. Furthermore, U.S. Pat. Nos. 5,654,468 and 5,569,674 disclose certain lipid lowering agents, namely, heteroacetic acid derivatives, which compete with radiolabeled $T_3$ in binding assays using rat liver nuclei and plasma membrane preparations. Still further, certain oxamic acids and derivatives thereof are known in the art, e.g., U.S. Pat. No. 4,069,343 describes the use of oxamic acids in preventing immediate type hypersensitivity reactions, U.S. Pat. No. 4,554,290 describes the use of oxamic acids to control pests on animals and plants, U.S. Pat. No. 5,232,947 describes the use of oxamic acids to improve damaged cerebral functions of the brain, and European Application Publication No. EP 0 580 550 (also U.S. Pat. No. 5,401,772) discloses oxamic acid derivatives as hypocholesterolemic agents. In addition, certain oxamic acid derivatives of thyroid hormones are known in the art. See, for example, Yokoyama et al., *J. Med. Chem.,* 38 (4), 695–707 (1995), Steele et al., International Congressional Service (Atherosclerosis X) 106, 321–324 (1995), and Stephan et al., Atherosclerosis, 126, 53–63 (1996).

Obesity is a major health risk that leads to increased mortality and incidence of Type 2 diabetes mellitus, hypertension, and dyslipidemia. In the United States, more than 50% of the adult population is overweight, and almost ¼ of the population is considered to be obese. The incidence of obesity is increasing in the United States at a three-percent cumulative annual growth rate. While the vast majority of obesity occurs in the United States and Europe, the prevalence of obesity is also increasing in Japan. The prevalence of obesity in adults is 10–20% in most countries of western Europe. Furthermore, obesity is a devastating disease which can also wreak havoc on an individual's mental health and self-esteem, which can ultimately affect a person's ability to interact socially with others. Unfortunately, the precise etiology of obesity is complex and poorly understood, and societal stereotypes and presumptions regarding obesity only tend to exacerbate the psychological effects of the disease. Because of the impact of obesity on society in general, much effort has been expended in efforts to treat obesity, however, success in the long-term treatment and/or prevention thereof remains elusive.

The thyroid receptor ligands of the present invention can be used to treat obesity, overweight condition, hyperlipidemia, glaucoma, cardiac arrhythmias (including atrial and ventricular arrhythmias), skin disorders, thyroid disease, hypothyroidism, thyroid cancer, diabetes, atherosclerosis, hypertension, coronary heart disease, congestive heart failure, hypercholesterolemia, depression, and osteoporosis.

The diabetic disease state is characterized by an impaired glucose metabolism that manifests itself in, inter alia, elevated glucose levels in patients suffering therefrom. Generally, diabetes is classified into two distinct subgroups:

(1) Type 1 diabetes, or insulin-dependent diabetes mellitus (IDDM), which arises when patients lack β-cells producing insulin in their pancreatic glands, and (2) Type 2 diabetes, or non-insulin dependent diabetes mellitus (NIDDM), which occurs in patients with, inter alia, impaired β-cell function.

At present, Type 1 diabetic patients are treated with insulin, while the majority of Type 2 diabetic patients are treated with hypoglycemic agents, such as sulfonylureas that stimulate β-cell function, with other agents that enhance the tissue selectivity of the patients towards insulin, or with insulin itself. Unfortunately, the use of insulin currently requires multiple daily doses, normally administered by self-injection, with determination of the proper dosage of insulin requiring frequent estimations of the sugar in urine or blood, performed either by the patient or the administering physician. The unintended administration of an excess dose of insulin can result in hypoglycemia, with adverse effects ranging from mild abnormalities in blood glucose to coma, or even death. Although hypoglycemic agents agents such as sulfonylureas have been employed widely in the treatment of NIDDM, this treatment is, in many instances, not completely satisfactory. In a large number of NIDDM patients, sulfonylureas have proven ineffective in normalizing blood sugar levels of patients, thereby leading to an increased risk of acquiring diabetic complications. Also, many patients gradually lose the ability to respond to treatment with sulfonylureas and are thus gradually forced into insulin treatment. Since many extant forms of diabetic therapy have proven ineffective achieving satisfactory glycemic control, there continues to be a great demand for novel therapeutic approaches.

Atherosclerosis, a disease of the arteries, is recognized to be a significant risk factor in the cause of death in the United States and Western Europe. The pathological sequence leading to atherosclerosis and occlusive heart disease is well established. The earliest stage in this sequence is the formation of so-called "fatty streaks" in the carotid, coronary and cerebral arteries and in the aorta. These lesions are yellow in color due to the presence of lipid deposits found principally within smooth-muscle cells and in macrophages of the intima layer of the arteries and aorta. It is further postulated that most of the cholesterol found within the fatty streaks, in turn, give rise to development of so-called "fibrous plaques," which consist of accumulated intimal smooth muscle cells laden with lipid which are surrounded by extra-cellular lipid, collagen, elastin and proteoglycans. The cells plus their matrix form a fibrous cap covering a deeper deposit of cell debris and additional extra-cellular lipid, comprising primarily free and esterified cholesterol. The fibrous plaque accumulates gradually, and is likely in time to become calcified and necrotic, advancing to a so-called "complicated lesion," which accounts for arterial occlusion and tendency toward mural thrombosis and arterial muscle spasm characterizing the condition of advanced atherosclerosis.

Epidemiological evidence has firmly established hyperlipidemia as a primary risk factor in causing cardiovascular disease (CVD) due to atherosclerosis. In recent years, medical professionals have placed a renewed emphasis on lowering plasma cholesterol levels, particularly low-density lipoprotein cholesterol, as an essential step in prevention of CVD. The upper limits of normal plasma cholesterol levels are now known to be significantly lower than heretofore appreciated. As a result, large segments of Western populations are now realized to be at particularly high risk. Such independent risk factors include glucose intolerance, left ventricular hypertrophy, hypertension, particularly affecting members of the male population. Cardiovascular disease is especially prevalent among diabetic subjects, at least in part because of the existence of multiple independent risk factors in this population. Successful treatment of hyperlipidemia in the general population and, in particular, diabetic individuals, is therefore of exceptional medical importance.

Hypertension, or high blood pressure, is a condition that occurs in the human population as a condition ancillary to various other disorders such as renal artery stenosis, pheochromocytoma or endocrine disorders. However, hypertension is also evidenced in many patients in whom the causative agent or disorder is unknown. While such so-called "essential" hypertension is often associated with disorders such as obesity, diabetes and hypertriglyceridemia, the relationship between these disorders has not yet been elucidated. Additionally, many patients display the symptoms of high blood pressure in the complete absence of any other signs of disease or disorder.

It is known that hypertension can directly lead to heart failure, renal failure and stroke, i.e. brain hemorrhaging, which conditions are capable of causing immediate death in a patient. Hypertension can also contribute to the development of atherosclerosis and coronary disease which conditions gradually weaken a patient and can also lead to death.

The exact cause of essential hypertension is unknown, though a number of factors are believed to contribute to the onset of the disease. Among such factors are stress, uncontrolled emotions, unregulated hormone release, especially those affecting the renin, angiotensin, and aldosterone systems, excessive salt and water due to kidney malfunction, wall thickening and hypertrophy of the vasculature resulting in constricted blood vessels, and certain genetic factors.

The treatment of essential hypertension has been undertaken bearing the foregoing factors in mind. Thus, a broad range of beta-blockers, vasoconstrictors, angiotensin converting enzyme (ACE) inhibitors and the like have been developed and marketed as antihypertensives. The treatment of hypertension utilizing these compounds has proven beneficial in the prevention of short-interval deaths such as heart failure, renal failure and brain hemorrhaging.

Hypertension has been associated with elevated blood insulin levels, a condition known as hyperinsulinemia. Insulin, a peptide hormone whose primary actions are to promote glucose utilization, protein synthesis and the formation and storage of neutral lipids, also acts, inter alia, to promote vascular cell growth and increase renal sodium retention. These latter functions, which are known causes of hypertension, can be accomplished without affecting glucose levels. Peripheral vasculature growth, for example, can cause constriction of peripheral capillaries while sodium retention increases blood volume. Thus, the lowering of insulin levels in hyperinsulinemics can prevent abnormal vascular growth and renal sodium retention caused by high insulin levels, thereby alleviating hypertension.

SUMMARY OF THE INVENTION

The instant invention provides certain thiazolidinedione, oxadiazolidinedione, and triazolone compounds of structural Formula (I), the stereoisomers and prodrugs thereof, and the pharmaceutically acceptable salts of the compounds, stereoisomers, and prodrugs, which are thyroid receptor ligands, wherein $R^1$, $R^2$, $R^3$, $R^4$, $R^5$, $R^6$, W, and X are as defined hereinbelow.

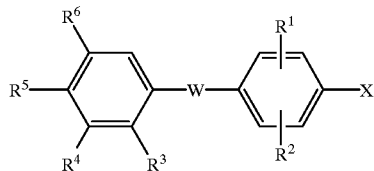

(I)

The invention further provides pharmaceutical compositions and kits comprising such compounds and methods of using such compounds, pharmaceutical compositions, and kits in the treatment of obesity, overweight condition, hyperlipidemia, glaucoma, cardiac arrhythmias (including atrial and ventricular arrhythmias), skin disorders, thyroid disease, hypothyroidism, thyroid cancer, diabetes, atherosclerosis, hypertension, coronary heart disease, congestive heart failure, hypercholesterolemia, depression, and osteoporosis.

DETAILED DESCRIPTION OF THE INVENTION

The present invention provides compounds of structural Formula (I)

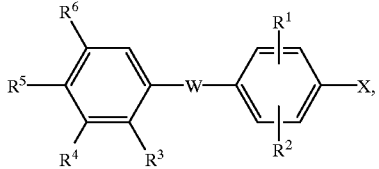

(I)

the stereoisomers and prodrugs thereof, and the pharmaceutically acceptable salts of the compounds, stereoisomers, and prodrugs, wherein:

W is oxygen, sulfur, —SO—, —S(O)$_2$, —CH$_2$—, —CF$_2$—, —CHF—, —C(O)—, —CH(OH)—, —NR$^a$, or —C(=CH$_2$)—;

$R^1$, $R^2$, $R^3$, and $R^6$ are each independently hydrogen, halogen, —(C$_1$-C$_8$)alkyl, —CF$_3$, —OCF$_3$, —O(C$_1$-C$_8$)alkyl, or —CN;

$R^4$ is hydrogen, —(C$_1$-C$_{12}$)alkyl substituted with zero to three substituents independently selected from Group V, —(C$_2$-C$_{12}$)alkenyl, —(C$_2$-C$_{12}$)alkynyl, halogen, —CN, —OR$^b$, —SR$^c$, —S(O)R$^c$, —S(O)$_2$R$^c$, aryl, heteroaryl, —(C$_3$-C$_{10}$)cycloalkyl, heterocycloalkyl, —S(O)$_2$NR$^c$R$^d$, —C(O)NR$^c$R$^d$, —C(O)OR$^c$, —NR$^a$C(O)R$^d$, —NR$^a$C(O)NR$^c$R$^d$, —NR$^a$S(O)$_2$R$^d$, or —C(O)R$^c$; or $R^3$ and $R^4$ are taken together along with the carbon atoms to which they are attached to form a carbocyclic ring of formula —(CH$_2$)$_i$— or a heterocyclic ring of formula —(CH$_2$)$_k$—Q—(CH$_2$)$_l$— wherein Q is oxygen, sulfur, or —NR$^e$—; i is 3, 4, 5, or 6; k is 0, 1, 2, 3, 4, or 5; and l is 0, 1, 2, 3, 4, or 5; and wherein the carbocyclic ring and the heterocyclic ring are each substituted with zero to four substituents independently selected from —(C$_1$-C$_4$)alkyl, —OR$^b$, oxo, —CN, phenyl, or —NR$^a$R$^g$;

$R^5$ is hydroxy, —O(C$_1$-C$_6$)alkyl, —OC(O)R$^f$, fluorine, or —C(O)OR$^c$; or $R^4$ and $R^5$ are taken together along with the carbon atoms to which they are attached to form a heterocyclic ring selected from the group consisting of —CR$^c$=CR$^a$—NH—, —N=CR$^a$—NH, —CR$^c$=CR$^a$—O—, —CR$^c$=CR$^a$—S—, —CR$^c$=N—NH—, and —CR$^a$=CR$^a$—CR$^a$=N—;

$R^a$ for each occurence is independently hydrogen, or —(C$_1$-C$_6$)alkyl substituted with zero or one —(C$_3$-C$_6$)cycloalkyl or methoxy;

$R^b$ for each occurence is independently hydrogen, —(C$_1$-C$_{12}$)alkyl substituted with zero to three substituents independently selected from Group V, aryl, heteroaryl, —(C$_3$-C$_{10}$)cycloalkyl, heterocycloalkyl, —C(O)NR$^c$R$^d$, or —C(O)R$^f$;

$R^c$ and $R^d$ for each occurence are each independently hydrogen, —(C$_1$-C$_{12}$)alkyl substituted with zero to three substituents independently selected from Group VI, —(C$_2$-C$_{12}$)alkenyl, —(C$_2$-C$_{12}$)alkynyl, aryl, heteroaryl, —(C$_3$-C$_{10}$)cycloalkyl, or heterocycloalkyl;

provided that when $R^4$ is the moiety —SR$^c$, —S(O)R$^c$, or —S(O)$_2$R$^c$, R$^c$ is other than hydrogen; or $R^c$ and $R^d$ are taken together along with the atom(s) to which they are attached to form a 3–10 membered heterocylic ring which may optionally contain a second heterogroup selected from oxygen, —NR$^e$—, or sulfur; and wherein the heterocyclic ring is substituted with zero to four substituents independently selected from —(C$_1$-C$_4$)alkyl, —OR$^b$, oxo, —CN, phenyl, or —NR$^a$R$^g$;

$R^e$ for each occurence is hydrogen, —CN, —(C$_1$-C$_{10}$)alkyl substituted with zero to three substituents independently selected from Group V, —(C$_2$-C$_{10}$)alkenyl, —(C$_2$-C$_{10}$)alkoxy, —(C$_3$-C$_{10}$)cycloalkyl, aryl, heteroaryl, —C(O)R$^f$, —C(O)OR$^f$, —C(O)NR$^a$R$^f$, or —S(O)$_2$R$^f$;

$R^f$ for each occurence is independently —(C$_1$-C$_{10}$)alkyl substituted with zero to three substituents independently selected from Group VI, —(C$_2$-C$_{12}$)alkenyl, —(C$_2$-C$_{10}$)alkynyl, —(C$_3$-C$_{10}$)cycloalkyl, aryl, heteroaryl, or heterocycloalkyl;

$R^g$ for each occurence is independently hydrogen, —(C$_1$-C$_6$)alkyl, —(C$_2$-C$_6$)alkenyl, aryl, —C(O)R$^f$, —C(O)OR$^f$, —C(O)NR$^a$R$^f$, —S(O)$_2$R$^f$, or —(C$_3$-C$_8$)cycloalkyl;

Group V is halogen, —CF$_3$, —OCF$_3$, —OH, oxo, —(C$_1$-C$_6$)alkoxy, —CN, aryl, heteroaryl, —(C$_3$-C$_{10}$)cycloalkyl, heterocycloalkyl, —SR$^f$, —S(O)R$^f$, —S(O)$_2$R$^f$, —S(O)$_2$NR$^a$R$^f$, —NR$^a$R$^g$, or —C(O)NR$^a$R$^f$;

Group VI is halogen, hydroxy, oxo, —(C$_1$-C$_6$)alkoxy, aryl, heteroaryl, —(C$_3$-C$_8$)cycloalkyl, heterocycloalkyl, —CN, or —OCF$_3$;

provided that when $R^4$ is —(C$_1$-C$_{12}$)alkyl substituted with zero to three substituents independently selected from Group V wherein the Group V substituent is oxo, the oxo group is substituted on a carbon atom other than the C$_1$ carbon atom in —(C$_1$-C$_{12}$)alkyl;

aryl for each occurence is independently phenyl or naphthyl substituted with zero to four substituents independently selected from halogen, —(C$_1$-C$_6$)alkyl, —CN, —SR$^f$, —S(O)R$^f$, —S(O)$_2$R$^f$, —(C$_3$-C$_6$)cycloalkyl, —S(O)$_2$NR$^a$R$^f$, —NR$^a$R$^g$, —C(O)NR$^a$R$^f$, —OR$^b$, —perfluoro—(C$_1$-C$_4$)alkyl, or —COOR$^f$;

provided that when the substituent(s) on aryl are —SR$^f$, —S(O)R$^f$, —S(O)$_2$R$^f$, —S(O)$_2$NR$^a$R$^f$, —NR$^a$R$^g$, —C(O)NR$^a$R$^f$,—OR$^b$, or —COOR$^f$, the substituents R$^b$, R$^f$, and R$^g$, are other than aryl or heteroaryl;

heteroaryl for each occurence is independently a 5-, 6-, 7-, 8-, or 9-membered monocyclic or bicyclic ring having from one to three heteroatoms selected from O, N, or S;

wherein in the bicyclic ring, a monocyclic heteroaryl ring is fused to a benzene ring or to another heteroaryl ring, and having zero to three substituents independently selected from halogen, —($C_1$–$C_4$)alkyl, —$CF_3$, —$OR^b$, —$NR^aR^g$, or —$COOR^f$;

provided that when the substituent(s) on heteroaryl are —$NR^aR^g$, —$OR^b$, or —$COOR^f$, the substituents $R^b$, $R^f$, and $R^g$, are other than aryl or heteroaryl;

heterocycloalkyl for each occurence is independently a 4-, 5-, 6-, 7-, 8-, or 9-membered monocyclic or bicyclic cycloalkyl ring having from one to three heteroatoms selected from oxygen, —$NR^e$, or sulfur, and having zero to four substituents independently selected from —($C_1$–$C_4$)alkyl, —$OR^b$, oxo, —CN, phenyl, or —$NR^aR^g$; and X is

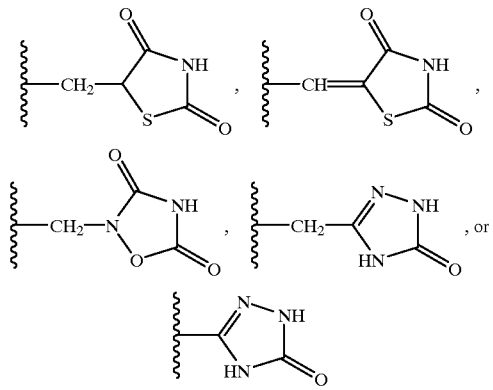

Preferably, the invention provides compounds of Formula (I), the stereoisomers and prodrugs thereof, and the pharmaceutically acceptable salts of the compounds, stereoisomers, and prodrugs, wherein W is oxygen.

More preferably, the invention provides compounds of Formula (I), the stereoisomers and prodrugs thereof, and the pharmaceutically acceptable salts of the compounds, stereoisomers, and prodrugs, wherein:

$R^1$ is located at the 3-position and $R^2$ is located at the 5-position, wherein $R^1$ and $R^2$ are each independently hydrogen, —($C_1$–$C_6$)alkyl, halogen, or —CN;

$R^3$ is hydrogen, —($C_1$–$C_4$)alkyl or halogen;

$R^4$ is —($C_1$–$C_{10}$)alkyl substituted with zero to three substituents independently selected from fluoro, hydroxy, oxo, aryl, heteroaryl, —($C_3$–$C_8$)cycloalkyl, or heterocycloalkyl, —$S(O)_2NR^cR^d$, —$C(O)NR^cR^d$, —$S(O)_2R^c$, —($C_3$–$C_8$)cycloalkyl, heterocycloalkyl, —$C(O)R^c$, —$OR^b$, —$SR^c$, —$S(O)R^c$, —$NR^aC(O)R^d$, —$NR^aC(O)NR^cR^d$, or —$NR^aS(O)_2R^d$; or $R^c$ and $R^d$ are taken together along with the atom(s) to which they are attached to form a 3–10 membered heterocylic ring which may optionally contain a second heterogroup selected from oxygen, —$NR^e$—, or sulfur; and wherein the heterocyclic ring is substituted with zero to four substituents independently selected from —($C_1$–$C_4$)alkyl, —$OR^b$, oxo, —CN, phenyl, or —$NR^aR^g$; or $R^3$ and $R^4$ are taken together along with the carbon atoms to which they are attached to form a carbocyclic ring of formula —$(CH_2)_n$— or a heterocyclic ring of formula —$(CH_2)_k$—Q—$(CH_2)_l$— wherein Q is —O—, —S— or —$NR^e$—; i is 3, 4, 5 or 6; k is 0, 1, 2, 3, 4 or 5; and l is 0, 1, 2, 3, 4 or 5; and wherein the carbocyclic ring and the heterocyclic ring are each substituted with zero to four substituents independently selected from —($C_1$–$C_4$)alkyl, —$OR^b$, oxo, —CN, phenyl, or —$NR^aR^g$;

provided that when $R^4$ is —($C_1$–$C_{10}$)alkyl substituted with zero to three substituents, the oxo group is substituted on a carbon atom other than the $C_1$ carbon atom in —($C_1$–$C_{10}$)alkyl;

$R^5$ is —OH, —$OC(O)R^f$, —$C(O)OR^c$, or —F; wherein $R^f$ is —($C_1$–$C_{10}$)alkyl substituted with zero to three substituents independently selected from Group VI;

$R^6$ is hydrogen, halogen or —($C_1$–$C_4$)alkyl; and

X is

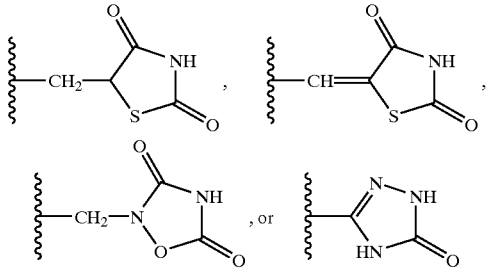

More preferably, the invention provides compounds of Formula (I), the stereoisomers and prod rugs thereof, and the pharmaceutically acceptable salts of the compounds, stereoisomers, and prod rugs, wherein:

$R^1$ and $R^2$ are each independently hydrogen, —($C_1$—$C_6$)alkyl, halogen, or —CN;

$R^3$ is hydrogen;

$R^4$ is —($C_1$–$C_{10}$)alkyl substituted with zero to three substituents independently selected from fluoro, hydroxy, oxo, aryl, heteroaryl, —($C_3$–$C_8$)cycloalkyl, or heterocycloalkyl, —$S(O)_2NR^cR^d$, —$C(O)NR^cR^d$, —$S(O)_2R^c$, —($C_3$–$C_8$)cycloalkyl, heterocycloalkyl, —$C(O)R^c$, —$OR^b$, —$SR^c$, —$S(O)R^c$, —$NR^aC(O)R^d$, —$NR^aC(O)NR^cR^d$, or —$NR^aS(O)_2R^d$; or $R^c$ and $R^d$ are taken together along with the atom(s) to which they are attached to form a 3–10 membered heterocylic ring which may optionally contain a second heterogroup selected from oxygen, —$NR^e$—, or sulfur; and wherein the heterocyclic ring is substituted with zero to four substituents independently selected from —($C_1$–$C_4$)alkyl, —$OR^b$, oxo, —CN, phenyl, or —$NR^aR^g$;

$R^5$ is —OH, fluoro, or —$OC(O)R^f$ wherein $R^f$ is —($C_1$–$C_{10}$)alkyl substituted with zero to three substituents independently selected from Group VI; and $R^6$ is hydrogen.

More preferably, the invention provides compounds of Formula (I), the stereoisomers and prodrugs thereof, and the pharmaceutically acceptable salts of the compounds, stereoisomers, and prodrugs, wherein:

$R^1$ and $R^2$ are both methyl, bromo, or chloro;

$R^4$ is —($C_1$–$C_{10}$)alkyl, substituted with zero to two substituents independently selected from fluoro, hydroxy, oxo, aryl, heteroaryl, —($C_3$–$C_8$)cycloalkyl, or heterocycloalkyl, —$S(O)_2NR^cR^d$, —$C(O)NR^cR^d$, —$S(O)_2R^c$, —($C_3$–$C_8$)cycloalkyl, heterocycloalkyl, —$C(O)R^c$, —$OR^b$, —$SR^c$, —$S(O)R^c$, —$NR^aC(O)R^d$, —$NR^aC(O)NR^cR^d$, or —$NR^aS(O)_2R^d$; or $R^c$ and $R^d$ are taken together along with the atom(s) to which they are attached to form a 3–10 membered heterocylic ring which may optionally contain a second heterogroup selected from oxygen, —$NR^e$—, or sulfur; and wherein the heterocyclic ring is substituted with zero to four substituents independently selected from —($C_1$–$C_4$)alkyl, —$OR^b$, oxo, —CN, phenyl, or —$NR^aR^g$; and $R^5$ is —OH.

The following compounds of Formula (I), the stereoisomers and prodrugs thereof, and the pharmaceutically acceptable salts of the compounds, stereoisomers, and prodrugs, are especially preferred in the practice of the pharmaceutical compositions, methods, and kits of the instant invention which pharmaceutical compositions, methods, and kits are described in further detail hereinbelow:

5-[3,5-dichloro-4-(4-hydroxy-3-isopropyl-phenoxy)-benzyl]-thiazolidine-2,4-dione;

5-[4-(4-hydroxy-3-isopropyl-phenoxy)-3,5-dimethyl-benzlidene]-thiazolidine-2,4-dione;

5-[4-(4-hydroxy-3-isopropyl-phenoxy)-3,5-dimethyl-benzyl]-thiazolidine-2,4-dione;

N-cyclopropyl-5-[2,6-dichloro-4-(2,4-dioxo-thiazolidin-5ylmethyl)-phenoxy]-2-hydroxy-benzenesulfonamide;

N-cyclobutyl-5-[2,6-dichloro-4-(2,4-dioxo-thiazolidin-5ylmethyl)-phenoxy]-2-hydroxy-N-methyl-benzamide;

2-[3,5-dichloro-4-(4-hydroxy-3-isopropyl-phenoxy)-benzyl]-[1,2,4]oxadiazolidine-3,5-dione;

2-[4-(3-isopropyl-4-methoxy-phenoxy)-3,5-dimethyl-benzyl]-[1,2,4]oxadiazolidine-3,5-dione;

2-[4-(4-hydroxy-3-isopropyl-phenoxy)-3,5-dimethyl-benzyl]-[1,2,4]oxadiazolidine-3,5-dione; and 5-[4-(4-hydroxy-3-isopropyl-phenoxy)-3,5-dimethyl-phenyl]-2,4-dihydro-[1,2,4]triazol-3-one.

The invention further provides pharmaceutical compositions and kits comprising the compounds of Formula (I), the stereoisomers and prodrugs thereof, and the pharmaceutically acceptable salts of the compounds, stereoisomers, and prodrugs, and to methods of the using the compounds, stereoisomers, and prodrugs, and the pharmaceutically acceptable salts thereof, in the treatment of obesity, overweight condition, hyperlipidemia, glaucoma, cardiac arrhythmias (including atrial and ventricular arrhythmias), skin disorders, thyroid disease, hypothyroidism, thyroid cancer, diabetes, atherosclerosis, hypertension, coronary heart disease, congestive heart failure, hypercholesterolemia, depression, and osteoporosis.

In particular, the present invention provides methods of treating a condition selected from the group consisting of obesity, overweight condition, hyperlipidemia, glaucoma, cardiac arrhythmias, skin disorders, thyroid disease, hypothyroidism, thyroid cancer, diabetes, atherosclerosis, hypertension, coronary heart disease, congestive heart failure, hypercholesteremia, depression and osteoporosis, in a mammal which comprises administering to said mammal a therapeutically effective amount of a compound of Formula (I), a stereoisomer or prodrug thereof, or a pharmaceutically acceptable salt of the compound, stereoisomer or prodrug. More preferably, the present invention provides such methods wherein the condition is obesity. More preferably, the present invention provides such methods wherein the condition is diabetes.

In addition, the present invention provides methods of inducing weight loss in a mammal which methods comprise administering to said mammal a therapeutically effective amount of a compound of Formula (I), a stereoisomer or prodrug thereof, or a pharmaceutically acceptable salt of the compound, stereoisomer or prodrug.

The present invention also provides methods of increasing energy expenditure in a mammal which methods comprise administering to said mammal a therapeutically effective amount of a compound of Formula (I), a stereoisomer or prodrug thereof, or a pharmaceutically acceptable salt of the compound, stereoisomer or prodrug.

In addition, the present invention provides methods of treating a condition selected from the group consisting of obesity, overweight condition, hyperlipidemia, glaucoma, cardiac arrhythmias, skin disorders, thyroid disease, hypothyroidism, thyroid cancer, diabetes, atherosclerosis, hypertension, coronary heart disease, congestive heart failure, hypercholesteremia, depression and osteoporosis, which methods comprise administering to a patient having or at risk of having a condition selected from the group consisting of obesity, overweight condition, hyperlipidemia, glaucoma, cardiac arrhythmias, skin disorders, thyroid disease, hypothyroidism, thyroid cancer, diabetes, atherosclerosis, hypertension, coronary heart disease, congestive heart failure, hypercholesteremia, depression and osteoporosis, a therapeutically effective amount of:

1) a compound of Formula (I), a stereoisomer or prodrug thereof, or a pharmaceutically acceptable salt of the compound, stereoisomer or prodrug, as defined hereinabove; and 2) an additional compound useful for treating a condition selected from the group consisting of obesity, overweight condition, hyperlipidemia, glaucoma, cardiac arrhythmias, skin disorders, thyroid disease, hypothyroidism, thyroid cancer, diabetes, atherosclerosis, hypertension, coronary heart disease, congestive heart failure, hypercholesteremia, depression and osteoporosis. More preferably, the present invention provides such methods wherein the condition is obesity. More preferably, the present invention provides such methods wherein the additional compound is a lipase inhibitor. Most preferably, the present invention provides such methods wherein the lipase inhibitor is selected from the group consisting of lipstatin, tetrahydrolipstatin (orlistat), FL-386, WAY-121898, Bay-N-3176, valilactone, esterastin, ebelactone A, ebelactone B and RHC 80267, stereoisomers thereof, and pharmaceutically acceptable salts of said compounds and stereoisomers. Also, more preferably, the present invention provides such methods wherein the additional compound is an anorectic agent. Most preferably, the present invention provides such methods wherein the anorectic agent is selected from the group consisting of phentermine, sibutramine, fenfluramine, dexfenfluramine and bromocriptine.

In another aspect, the present invention provides pharmaceutical compositions comprising a compound of Formula (I), a stereoisomer or prodrug thereof, or a pharmaceutically acceptable salt of the compound, stereoisomer or prodrug.

In another aspect, the invention provides kits for treating a condition selected from the group consisting of obesity, overweight condition, hyperlipidemia, glaucoma, cardiac arrhythmias, skin disorders, thyroid disease, hypothyroidism, thyroid cancer, diabetes, atherosclerosis, hypertension, coronary heart disease, congestive heart failure, hypercholesteremia, depression and osteoporosis, which kits comprise:

a) a first pharmaceutical composition comprising a compound of Formula (I), a stereoisomer or prodrug thereof, or a pharmaceutically acceptable salt of the compound, stereoisomer or prodrug, as defined hereinabove;

b) a second pharmaceutical composition comprising an additional compound useful for treating a condition selected from the group consisting of obesity, overweight condition, hyperlipidemia, glaucoma, cardiac arrhythmias, skin disorders, thyroid disease, hypothyroidism, thyroid cancer, diabetes, atherosclerosis, hypertension, coronary heart disease, congestive heart failure, hypercholesteremia, depression and osteoporosis; and c) a container.

In yet another aspect, the present invention provides pharmaceutical compositions comprising a compound of Formula (I), a stereoisomer or prodrug thereof, or a pharmaceutically acceptable salt of the compound, stereoisomer or prodrug, as defined hereinabove; and an additional compound useful to treat a condition selected from the group consisting of obesity, overweight condition, hyperlipidemia, glaucoma, cardiac arrhythmias, skin disorders, thyroid disease, hypothyroidism, thyroid cancer, diabetes, atherosclerosis, hypertension, coronary heart disease, congestive heart failure, hypercholesteremia, depression and osteoporosis.

More preferably, the present invention provides such compositions wherein the condition is obesity. More preferably, the present invention provides such compositions wherein the additional compound is a lipase inhibitor. Most preferably, the present invention provides such compositions wherein the lipase inhibitor is selected from the group consisting of lipstatin, tetrahydrolipstatin (orlistat), FL-386, WAY-121898, Bay-N-3176, valilactone, esterastin, ebelactone A, ebelactone B and RHC 80267, stereoisomers thereof, and pharmaceutically acceptable salts of said compounds and stereoisomers. In addition, more preferably, the present invention provides such compositions wherein the additional compound is an anorectic agent. Most preferably, the present invention provides such compositions wherein the anorectic agent is selected from the group consisting of phentermine, sibutramine, fenfluramine, dexfenfluramine and bromocriptine.

Also provided are methods of treating diabetes, which methods comprise administering to patients having, or at risk of having, diabetes, a therapeutically effective amount of a compound of Formula (I), a stereoisomer or prodrug thereof, or a pharmaceutically acceptable salt of the compound, stereoisomer, or prodrug.

In a preferred embodiment of the methods of treating diabetes, the diabetes is Type I diabetes.

In another preferred embodiment of the methods of treating diabetes, the diabetes is Type II diabetes.

Also provided are methods of treating atherosclerosis, which methods comprise administering to patients having, or at risk of having, atherosclerosis, a therapeutically effective amount of a compound of Formula (I), a stereoisomer or prodrug thereof, or a pharmaceutically acceptable salt of the compound, stereoisomer, or prodrug.

Also provided are methods of treating hypertension, which methods comprise administering to patients having, or at risk of having, hypertension, a therapeutically effective amount of a compound of Formula (I), a stereoisomer or prodrug thereof, or a pharmaceutically acceptable salt of the compound, stereoisomer, or prodrug.

Also provided are methods of treating coronary heart disease, which methods comprise administering to patients having, or at risk of having, coronary heart disease, a therapeutically effective amount of a compound of Formula (I), a stereoisomer or prodrug thereof, or a pharmaceutically acceptable salt of the compound, stereoisomer, or prodrug.

Also provided are methods of treating hypercholesterolemia, which methods comprise administering to patients having, or at risk of having, hypercholesterolemia, a therapeutically effective amount of a compound of Formula (I), a stereoisomer or prodrug thereof, or a pharmaceutically acceptable salt of the compound, stereoisomer, or prodrug.

Also provided are methods of treating hyperlipidemia, which methods comprise administering to patients having, or at risk of having, hyperlipidemia, a therapeutically effective amount of a compound of Formula (I), a stereoisomer or prodrug thereof, or a pharmaceutically acceptable salt of the compound, stereoisomer, or prodrug.

Also provided are methods of treating thyroid disease, which methods comprise administering to patients having, or at risk of having, thyroid disease, a therapeutically effective amount of a compound of Formula (I), a stereoisomer or prodrug thereof, or a pharmaceutically acceptable salt of the compound, stereoisomer, or prodrug.

Also provided are methods of treating hypothyroidism, which methods comprise administering to patients having, or at risk of having, hypothyroidism, a therapeutically effective amount of a compound of Formula (I), a stereoisomer or prodrug thereof, or a pharmaceutically acceptable salt of the compound, stereoisomer, or prodrug.

Also provided are methods of treating depression, which methods comprise administering to patients having, or at risk of having, depression, a therapeutically effective amount of a compound of Formula (I), a stereoisomer or prodrug thereof, or a pharmaceutically acceptable salt of the compound, stereoisomer, or prodrug.

Also provided are methods of treating obesity, which methods comprise administering to obese patients, or patients at risk of becoming obese, a therapeutically effective amount of a compound of Formula (I), a stereoisomer or prodrug thereof, or a pharmaceutically acceptable salt of the compound, stereoisomer, or prodrug.

Also provided are methods of treating osteoporosis, which methods comprise administering to patients having, or at risk of having, osteoporosis, a therapeutically effective amount of a compound of Formula (I), a stereoisomer or prodrug thereof, or a pharmaceutically acceptable salt of the compound, stereoisomer, or prodrug.

Also provided are methods of treating thyroid cancer, which methods comprise administering to patients having, or at risk of having, thyroid cancer, a therapeutically effective amount of a compound of Formula (I), a stereoisomer or prodrug thereof, or a pharmaceutically acceptable salt of the compound, stereoisomer, or prodrug.

Also provided are methods of treating glaucoma, which methods comprise administering to patients having, or at risk of having, glaucoma, a therapeutically effective amount of a compound of Formula (I), a stereoisomer or prodrug thereof, or a pharmaceutically acceptable salt of the compound, stereoisomer, or prodrug.

Also provided are methods of treating cardiac arrhythmias, which methods comprise administering to patients having, or at risk of having, cardiac arrhythmias, a therapeutically effective amount of a compound of Formula (I), a stereoisomer or prodrug thereof, or a pharmaceutically acceptable salt of the compound, stereoisomer, or prodrug.

Also provided are methods of treating congestive heart failure, which methods comprise administering to patients having, or at risk of having, congestive heart failure, a therapeutically effective amount of a compound of Formula (I), a stereoisomer or prodrug thereof, or a pharmaceutically acceptable salt of the compound, stereoisomer, or prodrug.

The compounds of the invention may be named according to the IUPAC (International Union for Pure and Applied Chemistry) or CAS (Chemical Abstracts Service) nomenclature systems.

In a preferred manner of naming the compounds of the instant invention, the carbon atoms in the respective rings are numbered as depicted in the following structure (II):

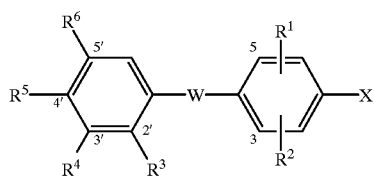

(II)

The carbon atom content of the various hydrocarbon-containing moieties is indicated by a prefix designating the minimum and maximum number of carbon atoms in the moiety, i.e. the prefix ($C_i$–$C_j$) indicates a moiety of the integer "i" to "j" carbon atoms, inclusive. Thus, for example, ($C_1$–$C_3$)alkyl refers to alkyl of one to three carbon atoms inclusive, or methyl, ethyl, propyl, isopropyl, and all isomeric forms, and straight and branched forms thereof.

The term "alkyl" denotes a straight or branched chain hydrocarbon. Representative examples of alkyl groups comprise methyl, ethyl, propyl, isopropyl, butyl, isobutyl, tert-butyl, sec-butyl, pentyl, and hexyl. Generally preferred alkyl groups are ($C_1$–$C_{12}$)alkyl.

The term "alkoxy" denotes an alkyl group bonded to an oxygen atom. Representative examples of alkoxy groups include methoxy, ethoxy, tert-butoxy, propoxy, and isobutoxy. Preferred alkoxy groups are ($C_1$–$C_{12}$)alkoxy.

The term "halogen" or "halo" denotes a radical derived from chlorine, fluorine, bromine, or iodine.

The term "alkenyl" denotes a branched or straight chain hydrocarbon having one or more carbon-carbon double bonds.

The term "alkynyl" denotes a branched or straight chain hydrocarbon having one or more carbon-carbon triple bonds.

The term "cycloalkyl" denotes a cyclic hydrocarbon. Examples of cycloalkyl groups include cyclopropyl, cyclobutyl, cyclopentyl, cyclohexyl, and cycloheptyl. Preferred cycloalkyl groups are ($C_3$–$C_{10}$)cyloalkyl. It is also possible for the cycloalkyl group to have one or more double bonds or triple bonds, or a combination of double bonds and triple bonds, but is not aromatic. Examples of cycloalkyl groups having a double or triple bond include cyclopentenyl, cyclohexenyl, cyclohexadienyl, cyclobutadienyl, and the like. It is also noted that the term cycloalkyl includes polycyclic compounds such as bicyclic or tricyclic compounds. The cycloalkyl groups may be substituted or unsubsituted with from one to four substituents.

The term "perfluoroalkyl" denotes an alkyl group in which all of the hydrogen atoms have been replaced with fluorine atoms.

The term "acyl" denotes a group derived from an organic acid (—COOH) by removal of the hydroxy group (—OH).

The term "aryl" denotes a cyclic, aromatic hydrocarbon. Examples of aryl groups include phenyl, naphthyl and biphenyl. The aryl group can be unsubstituted or substituted.

The term "heteroatom" includes oxygen, nitrogen, sulfur, and phosphorous.

The term "heteroaryl" denotes a cyclic, aromatic hydrocarbon in which one or more carbon atoms have been replaced with heteroatoms. If the heteroaryl group contains more than one heteroatom, the heteroatoms may be the same or different. Examples of heteroaryl groups include pyridyl, pyrimidinyl, imidazolyl, thienyl, furyl, pyrazinyl, pyrrolyl, pyranyl, isobenzofuranyl, chromenyl, xanthenyl, indolyl, isoindolyl, indolizinyl, triazolyl, pyridazinyl, indazolyl, purinyl, quinolizinyl, isoquinolyl, quinolyl, phthalazinyl, naphthyridinyl, quinoxalinyl, isothiazolyl, and benzo[b]thienyl. Preferred heteroaryl groups are five and six membered rings and contain from one to three heteroatoms independently selected from O, N, and S. The heteroaryl group, including each heteroatom, can be unsubstituted or substituted with from 1 to 4 substituents, as chemically feasible. For example, the heteroatom S may be substituted with one or two oxo groups, which may be shown as =O.

The term "heterocycloalkyl" denotes a cycloalkyl group in which one or more of the carbon atoms has been replaced with heteroatoms. If the heterocycloalkyl group contains more than one heteroatom, the heteroatoms may be the same or different. Examples of heterocycloalkyl groups include tetrahydrofuryl, morpholinyl, piperazinyl, piperidyl, and pyrrolidinyl. Preferred heterocycloalkyl groups are five and six membered rings and contain from one to three heteroatoms independently selected from O, N, and S. It is also possible for the heterocycloalkyl group to have one or more double bonds or triple bonds or a combination of double bonds and triple bonds, but it is not aromatic. Examples of heterocycloalkyl groups containing double or triple bonds include dihydrofuran, and the like. A heterocycloalkyl group, including each heteroatom, can be unsubstituted or substituted with from 1 to 4 substituents, as chemically feasible. For example, the heteroatom S may be substituted with one or two oxo groups, which may be shown as =O.

It is also noted that the cyclic ring groups, i.e., aryl, heteroaryl, cycloalkyl, heterocycloalkyl, can comprise more than one ring. For example, the naphthyl group is a fused bicyclic ring system. It is also intended that the present invention include ring groups that have bridging atoms, or ring groups that have a spiro orientation. For example, "spirocycloalkyl" means a cycloalkyl ring having a spiro union (the union formed by a single atom which is the only common member of the rings). In addition, it is understood that, unless specifically noted otherwise, all suitable isomers of the cyclic ring groups are included herein.

Representative examples of five to six membered aromatic rings, optionally having one or two heteroatoms, are phenyl, furyl, thienyl, pyrrolyl, oxazolyl, thiazolyl, imidazolyl, pyrazolyl, isoxazolyl, isothiazolyl, pyridinyl, pyridiazinyl, pyrimidinyl, and pyrazinyl.

Representative examples of partially saturated, fully saturated or fully unsaturated five to eight membered rings, optionally having one to three heteroatoms, are cyclopentyl, cyclohexyl, cycloheptyl, cyclooctyl and phenyl. Further exemplary five membered rings are furyl, thienyl, pyrrolyl, 2-pyrrolinyl, 3-pyrrolinyl, pyrrolidinyl, 1,3-dioxolanyl, oxazolyl, thiazolyl, imidazolyl, 2H-imidazolyl, 2-imidazolinyl, imidazolidinyl, pyrazolyl, 2-pyrazolinyl, pyrazolidinyl, isoxazolyl, isothiazolyl, 1,2-dithiolyl, 1,3-dithiolyl, 3H-1,2-oxathiolyl, 1,2,3-oxadizaolyl, 1,2,4-oxadiazolyl, 1,2,5-oxadiazolyl, 1,3,4-oxadiazolyl, 1,2,3-triazolyl, 1,2,4-trizaolyl, 1,3,4-thiadiazolyl, 3H-1,2,3-dioxazolyl, 1,2,4-dioxazolyl, 1,3,2-dioxazolyl, 1,3,4-dioxazolyl, 5H-1,2,5-oxathiazolyl, and 1,3-oxathiolyl.

Further exemplary six membered rings are 2H-pyranyl, 4H-pyranyl, pyridinyl, piperidinyl, 1,2-dioxinyl, 1,3-dioxinyl, 1,4-dioxanyl, morpholinyl, 1,4-dithianyl, thiomorpholinyl, pyridazinyl, pyrimidinyl, pyrazinyl, piperazinyl, 1,3,5-triazinyl, 1,2,4-triazinyl, 1,2,3-triazinyl, 1,3,5-trithianyl, 4H-1,2-oxazinyl, 2H-1,3-oxazinyl, 6H-1,3-oxazinyl, 6H-1,2-oxazinyl, 1,4-oxazinyl, 2H-1,2-oxazinyl, 4H-1,4-oxazinyl, 1,2,5-oxathiazinyl, 1,4-oxazinyl, o-isoxazinyl, p-isoxazinyl, 1,2,5-oxathiazinyl, 1,2,6-oxathiazinyl, and 1,4,2-oxadiazinyl.

Further exemplary seven membered rings are azepinyl, oxepinyl, thiepinyl and 1,2,4-triazepinyl.

Further exemplary eight membered rings are cyclooctyl, cyclooctenyl and cyclooctadienyl.

Exemplary bicyclic rings consisting of two fused partially saturated, fully saturated or fully unsaturated five and/or six membered rings, taken independently, optionally having one to four heteroatoms are indolizinyl, indolyl, isoindolyl, indolinyl, cyclopenta(b)pyridinyl, pyrano(3,4-b)pyrrolyl, benzofuryl, isobenzofuryl, benzo(b)thienyl, benzo(c)thienyl, 1H-indazolyl, indoxazinyl, benzoxazolyl, anthranilyl, benzimidazolyl, benzthiazolyl, purinyl, quinolinyl, isoquinolinyl, cinnolinyl, phthalazinyl, quinazolinyl, quinoxalinyl, 1,8-naphthyridinyl, pteridinyl, indenyl, isoindenyl, naphthyl, tetralinyl, decalinyl, 2H-1-benzopyranyl, pyrido(3,4-b)-pyridinyl, pyrido(3,2-b)-pyridinyl, pyrido(4,3-b)-pyridinyl, 2H-1,3-benzoxazinyl, 2H-1,4-benzoxazinyl, 1 H-2,3-benzoxazinyl, 4H-3,1-benzoxazinyl, 2H-1,2-benzoxazinyl and 4H-1,4-benzoxazinyl.

A cyclic ring group may be bonded to another group in more than one way. If no particular bonding arrangement is specified, then all possible arrangements are intended. For example, the term "pyridyl" includes 2-, 3-, or 4-pyridyl, and the term "thienyl" includes 2-, or 3-thienyl.

The term "substituted" means that a hydrogen atom on a molecule has been replaced with a different atom or molecule. The atom or molecule replacing the hydrogen atom is called a substituent.

The symbol "–" represents a covalent bond.

The term "radical" denotes a group of atoms that behaves as a single atom in a chemical reaction, e.g., an organic radical is a group of atoms which confers characteristic properties on a compound containing it, or which remains unchanged during a series of reactions.

The phrase "therapeutically effective amount" means an amount of a compound of Formula (I), a stereoisomer or prodrug thereof, or a pharmaceutically acceptable salt of the compound, stereoisomer, or prodrug, or a combination of a compound of Formula (I), a stereoisomer, or prodrug thereof, or a pharmaceutically acceptable salt of the compound, stereoisomer, or prodrug, and another compound to be described in detail hereinbelow, which amount ameliorates, attenuates, or eliminates one or more symptoms of a particular disease or condition, or prevents or delays the onset of one of more symptoms of a particular disease or condition.

The term "patient" means animals, such as dogs, cats, cows, horses, sheep, and humans. Preferred patients are mammals, especially humans, including both male and female sexes.

The phrase "pharmaceutically acceptable" indicates that the substance or composition must be compatible chemically and/or toxicologically, with other ingredients comprising a formulation, and/or the patient being treated therewith.

The phrase "reaction-inert solvent" or "inert solvent" refers to a solvent or mixture of solvents that does not interact with starting materials, reagents, intermediates or products in a manner that adversely affects the desired product.

The terms "treating", "treat", or "treatment" embrace both preventative, i.e., prophylactic, and palliative treatment.

The characteristics of patients at risk of having atherosclerosis are well known to one of ordinary skill in the art and include patients who have a family history of cardiovascular disease, including hypertension and atherosclerosis, obesity, infrequency of exercise, hypercholesterolemia, hyperlipidemia and/or hypertriglyceridemia, high levels of low-density lipoprotein (LDL) or lipoprotein (a) (Lp(a)), low levels of high-density lipoprotein (HDL), and the like.

In one aspect, the present invention concerns the treatment of diabetes, including impaired glucose tolerance, insulin resistance, insulin dependent diabetes mellitus (Type I), and non-insulin dependent diabetes mellitus (NIDDM or Type II). Also included in the treatment of diabetes are diabetic complications related thereto, including neuropathy, nephropathy, retinopathy, cataracts, and the like.

The preferred type of diabetes to be treated by the compounds of Formula (I), the stereoisomers and prodrugs thereof, and the pharmaceutically acceptable salts of the compounds, stereoisomers, or prodrugs, is non-insulin dependent diabetes mellitus, i.e. NIDDM.

Diabetes can be treated by administering to a patient having diabetes (Type I or Type II), insulin resistance, impaired glucose tolerance, or any of the diabetic complications such as neuropathy, nephropathy, retinopathy or cataracts, a therapeutically effective amount of a compound of Formula (I), a stereoisomer, or prodrug thereof, or a pharmaceutically acceptable salt of the compound, stereoisomer, or prodrug. It is also intended that diabetic patients can be treated by administering a compound of Formula (I), a stereoisomer, or prodrug thereof, or a pharmaceutically acceptable salt of the compound, stereoisomer, or prodrug together with one or more anti-diabetic agents.

Representative agents that can be used to treat diabetes in combination with the compounds of Formula (I), the stereoisomers and prodrugs thereof, and the pharmaceutically acceptable salts of the compounds, stereoisomers, and prodrugs, include insulin and insulin analogs (e.g. LysPro insulin); inhaled insulin; GLP-1 (7–37) (insulinotropin) and GLP-1 (7–36)—NH$_2$; sulfonylureas and analogs: chlorpropamide, glibenclamide, tolbutamide, tolazamide, acetohexamide, glypizide, glimepiride, repaglinide, meglitinide; biguanides: metformin, phenformin, buformin; α2-antagonists and imidazolines: midaglizole, isaglidole, deriglidole, idazoxan, efaroxan, fluparoxan; other insulin secretagogues: linogliride, A-4166; glitazones: ciglitazone, pioglitazone, englitazone, troglitazone, darglitazone, BRL49653; fatty acid oxidation inhibitors: clomoxir, etomoxir; α-glucosidase inhibitors: acarbose, miglitol, emiglitate, voglibose, MDL-25,637, camiglibose, MDL-73, 945; β-agonists: BRL 35135, BRL 37344, RO 16-8714, ICI D7114, CL 316,243; phosphodiesterase inhibitors: L-386, 398; lipid-lowering agents: benfluorex; antiobesity agents: fenfluramine; vanadate and vanadium complexes (e.g. Naglivan®) and peroxovanadium complexes; amylin antagonists; glucagon antagonists; gluconeogenesis inhibitors; somatostatin analogs; antilipolytic agents: nicotinic acid, acipimox, WAG 994. Also intended to be used in combination with the compounds of Formula (I), the stereoisomers and prodrugs thereof, and the pharmaceutically acceptable salts of the compounds, stereoisomers, and prodrugs, are pramlintide (symlin™), AC 2993 and nateglinide. Any agent, or combination of agents, can be administered as described hereinabove.

In addition, the compounds of Formula (I), the stereoisomers and prodrugs thereof, and the pharmaceutically acceptable salts of the compounds, stereoisomers, and prodrugs, can be used in combination with one or more aldose reductase inhibitors, glycogen phosphorylase inhibitors, sorbitol dehydrogenase inhibitors, NHE-1 inhibitors and/or glucocorticoid receptor antagonists.

The compounds of Formula (I), the stereoisomers and prodrugs thereof, and the pharmaceutically acceptable salts of the compounds, stereoisomers, and prodrugs, can be used in combination with an aldose reductase inhibitor, which term refers to compounds inhibiting the bioconversion of glucose to sorbitol, a reaction catalyzed by the enzyme aldose reductase. Accordingly, aldose reductase inhibitors constitute a class of compounds that have become well known for their utility in preventing and treating conditions arising from complications of diabetes including, for example, diabetic neuropathy and nephropathy. Such compounds are well known to one of ordinary skill in the art and are readily identified by standard biological tests. For example, the aldose reductase inhibitor zopolrestat, 3,4-dihydro-4-oxo-3-[[5-(trifluoromethyl)-2-benzothiazolyl] methyl]-1-phthalazineacetic acid, and related compounds are described in U.S. Pat. No. 4,939,140.

Aldose reductase inhibitors are known to be useful in lowering lipid levels in mammals. See, for example, U.S. Pat. No. 4,492,706 and European Application Publication No. EP 0 310 931. U.S. Pat. No. 5,064,830 discloses the use of certain oxophthalazinyl acetic acid aldose reductase inhibitors, including zopolrestat, for lowering of blood uric acid levels. Commonly assigned U.S. Pat. No. 5,391,551 discloses the use of certain aldose reductase inhibitors, including zopolrestat, for lowering blood lipid levels in humans. The disclosure teaches that therapeutic utilities derive from the treatment of diseases caused by an increased level of triglycerides in the blood, such diseases include cardiovascular disorders such as thrombosis, arteriosclerosis, myocardial infarction, and angina pectoris. A preferred aldose reductase inhibitor disclosed therein is zopolrestat.

Any aldose reductase inhibitor may be used in combination with the compounds of Formula (I), the stereoisomers and prodrugs thereof, and the pharmaceutically acceptable salts of the compounds, stereoisomers, and prodrugs. Aldose reductase inhibition is readily determined by those skilled in the art according to standard assays (J. Malone, Diabetes, 29, 861–864 (1980) "Red Cell Sorbitol, an Indicator of Diabetic Control"). A variety of aldose reductase inhibitors are described herein, however, other aldose reductase inhibitors useful in the compositions and methods of this invention will be known to one of ordinary skill in the art.

The activity of an aldose reductase inhibitor in a particular tissue substrate can be determined by testing the amount of aldose reductase inhibitor that is required to lower tissue sorbitol (i.e., by inhibiting the further production of sorbitol consequent to blocking aldose reductase) or lower tissue fructose (by inhibiting the production of sorbitol consequent to blocking aldose reductase and consequently the production of fructose).

Accordingly, additional examples of aldose reductase inhibitors useful in the practice of the pharmaceutical compositions, combinations, methods, and kits of the present invention may comprise:

(1) 3-(4-bromo-2-fluorobenzyl)-3,4-dihydro-4-oxo-1-phthalazineacetic acid (ponalrestat, U.S. Pat. No. 4,251, 528);

(2) N-[[(5-trifluoromethyl)-6-methoxy-1-naphthalenyl] thioxomethyl]—N-methylglycine (tolrestat, U.S. Pat. No. 4,600,724);

(3) 5-[(Z,E)-β-methylcinnamylidene]4-oxo-2-thioxo-3-thiazolideneacetic acid (epalrestat, U.S. Pat. Nos. 4,464,382, 4,791,126, and 4,831,045);

(4) 3-(4-bromo-2-fluorobenzyl)-7-chloro-3,4-dihydro-2, 4-dioxo-1 (2H)-quinazolineacetic acid (zenarestat, U.S. Pat. Nos. 4,734,419 and 4,883,800);

(5) 2R,4R-6,7-dichloro-4-hydroxy-2-methylchroman-4-acetic acid (U.S. Pat. No. 4,883,410);

(6) 2R,4R-6,7-dichloro-6-fluoro-4-hydroxy-2-methylchroman-4-acetic acid (U.S. Pat. No. 4,883,410);

(7) 3,4-dihydro-2,8-diisopropyl-3-oxo-2H-1,4-benzoxazine-4-acetic acid (U.S. Pat. No. 4,771,050);

(8) 3,4-dihydro-3-oxo-4-[(4,5,7-trifluoro-2-benzothiazolyl)methyl]-2H-1,4-benzothiazine-2-acetic acid (SPR-210, U.S. Pat. No. 5,252,572);

(9) N-[3,5-dimethyl-4-[(nitromethyl)sulfonyl]phenyl]-2-methyl-benzeneacetamide (ZD5522, U.S. Pat. Nos. 5,270, 342 and 5,430,060);

(10) (S)-6-fluorospiro[chroman-4,4'-imidazolidine]-2,5'-dione (sorbinil, U.S. Pat. No. 4,130,714);

(11) d-2-methyl-6-fluoro-spiro(chroman-4',4'-imidazolidine)-2',5'-dione (U.S. Pat. No. 4,540,704);

(12) 2-fluoro-spiro(9H-fluorene-9,4'-imidazolidine)2',5'-dione (U.S. Pat. No. 4,438,272);

(13) 2,7-di-fluoro-spiro(9H-fluorene-9,4'-imidazolidine) 2',5'-dione (U.S. Pat. No. 4,436,745 and U.S. Pat. No. 4,438,272);

(14) 2,7-di-fluoro-5-methoxy-spiro(9H-fluorene-9,4'-imidazolidine)2',5'-dione (U.S. Pat. Nos. 4,436,745 and 4,438,272);

(15) 7-fluoro-spiro(5H-indenol[1,2-b]pyridine-5,3'-pyrrolidine)2,5'-dione (U.S. Pat. Nos. 4,436,745 and 4,438, 272);

(16) d-cis-6'-chloro-2',3'-dihydro-2'-methyl-spiro—(imidazolidine-4,4'-4'-H-pyrano(2,3-b)pyridine)-2,5-dione (U.S. Pat. No. 4,980,357);

(17) spiro[imidazolidine-4,5'(6H)-quinoline]2,5-dione-3'-chloro-7,'8'-dihydro-7'-methyl—(5'-cis) (U.S. Pat. No. 5,066,659);

(18) (2S,4S)-6-fluoro-2',5'-dioxospiro(chroman-4,4'-imidazolidine)-2-carboxamide (U.S. Pat. No. 5,447,946); and

(19) 2-[(4-bromo-2-fluorophenyl)methyl]-6-fluorospiro [isoquinoline-4(1 H),3'-pyrrolidine]-1,2',3,5'(2H)-tetrone (ARI-509, U.S. Pat. No. 5,037,831).

Other aldose reductase inhibitors useful in the practice of the pharmaceutical compositions, combinations, methods, and kits of the invention comprise compounds of structural Formula (Ia):

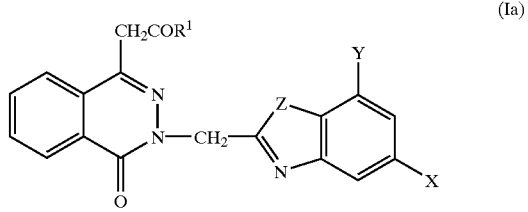

and the pharmaceutically acceptable salts and prodrugs thereof, wherein

Z is O or S;

$R^1$ is hydroxy or a group capable of being removed in vivo to produce a compound of Formula (Ia) wherein $R^1$ is OH; and X and Y are the same or different and are selected from hydrogen, trifluoromethyl, fluoro, and chloro.

A preferred subgroup within the above group of aldose reductase inhibitors includes numbered compounds 1, 2, 3, 4, 5, 6, 9, 10, and 17, and the following compounds of Formula (Ia):

3,4-dihydro-3-(5-fluorobenzothiazol-2-ylmethyl)-4-oxophthalazin-1-yl-acetic acid [$R^1$=hydroxy; X=F; Y=H];

3-(5,7-difluorobenzothiazol-2-ylmethyl)-3,4-dihydro-4-oxophthalazin-1-ylacetic acid [$R^1$=hydroxy; X=Y=F];

3-(5-chlorobenzothiazol-2-ylmethyl)-3,4-dihydro-4-oxophthalazin-1-ylacetic acid [$R^1$=hydroxy; X=Cl; Y=H];

3-(5,7-dichlorobenzothiazol-2-ylmethyl)-3,4-dihydro-4-oxophthalazin-1-ylacetic acid [$R^1$=hydroxy; X=Y=Cl];

3,4-dihydro-4-oxo-3-(5-trifluoromethylbenzoxazol-2-ylmethyl)phthalazin-1-ylacetic acid [$R^1$=hydroxy; X=$CF_3$; Y=H];

3,4-dihydro-3-(5-fluorobenzoxazol-2-ylmethyl)-4-oxophthalazin-1-yl-acetic acid [$R^1$=hydroxy; X=F; Y=H];

3-(5,7-difluorobenzoxazol-2-ylmethyl)-3,4-dihydro-4-oxophthalazin-1-ylacetic acid [$R^1$=hydroxy; X=Y=F];

3-(5-chlorobenzoxazol-2-ylmethyl)-3,4-dihydro-4-oxophthalazin-1-ylacetic acid [$R^1$=hydroxy; X=Cl; Y=H];

3-(5,7-dichlorobenzoxazol-2-ylmethyl)-3,4-dihydro-4-oxophthalazin-1-ylacetic acid [$R^1$=hydroxy; X=Y=Cl]; and zopolrestat; 1-phthalazineacetic acid, 3,4-dihydro-4-oxo-3-[[5-(trifluoromethyl)-2-benzothiazolyl]methyl]—[$R^1$=hydroxy; X=trifluoromethyl; Y=H].

Procedures for preparing the aldose reductase inhibitors of Formula (Ia) can be found in International Application Publication No. WO 99/26659.

The compounds of Formula (I), the stereoisomers and prodrugs thereof, and the pharmaceutically acceptable salts of the compounds, stereoisomers, and prodrugs, can also be used in combination with a glucocorticoid receptor antagonist.

The glucocorticoid receptor (GR) is present in glucocorticoid responsive cells where it resides in the cytosol in an inactive state until stimulatation by an agonist. Upon stimulation, the glucocorticoid receptor translocates to the cell nucleus where it specifically interacts with DNA and/or protein(s) and regulates transcription in a glucocorticoid-responsive manner. Two examples of proteins that interact with the glucocorticoid receptor are the transcription factors, API and NFκ-β. Such interactions result in the inhibition of API- and NFκ-β-mediated transcription and are believed to be responsible for the anti-inflammatory activity of endogenously administered glucocorticoids. In addition, glucocorticoids may also exert physiologic effects independent of nuclear transcription. Biologically relevant glucocorticoid receptor agonists include cortisol and corticosterone.

Many synthetic glucocorticoid receptor agonists exist including dexamethasone, prednisone and prednisilone. By definition, glucocorticoid receptor antagonists bind to the receptor and prevent glucocorticoid receptor agonists from binding and eliciting GR mediated events, including transcription. RU-486 is an example of a non-selective glucocorticoid receptor antagonist. GR antagonists can be used in the treatment of diseases associated with an excess, or deficiency, of glucocorticoids in the body. As such, they may be used to treat the following: obesity, diabetes, cardiovascular disease, hypertension, Syndrome X, depression, anxiety, glaucoma, human immunodeficiency virus (HIV) or acquired immunodeficiency syndrome (AIDS), neurodegeneration (for example, Alzheimer's and Parkinson's), cognition enhancement, Cushing's Syndrome, Addison's Disease, osteoporosis, frailty, inflammatory diseases (such as osteoarthritis, rheumatoid arthritis, asthma and rhinitis), tests of adrenal function, viral infection, immunodeficiency, immunomodulation, autoimmune diseases, allergies, wound healing, compulsive behavior, multi-drug resistance, addiction, psychosis, anorexia, cachexia, post-traumatic stress syndrome, post-surgical bone fracture, medical catabolism and prevention of muscle frailty.

Examples of preferred GR antagonists useful in the pharmaceutical compositions, combinations, methods, and kits of the invention, may comprise, inter alia, those compounds disclosed in commonly assigned U.S. Provisional Application No. 60/132,130, which is hereby incorporated by reference.

The compounds of Formula (I), the stereoisomers and prodrugs thereof, and the pharmaceutically acceptable salts of the compounds, stereoisomers, and prodrugs, can also be used in combination with a sorbitol dehydrogenase inhibitor.

Sorbitol dehydrogenase inhibitors lower fructose levels and have been used to treat or prevent diabetic complications such as neuropathy, retinopathy, nephropathy, cardiomyopathy, microangiopathy, and macroangiopathy. U.S. Pat. Nos. 5,728,704 and 5,866,578 disclose compounds and a method for treating or preventing diabetic complications by inhibiting the enzyme sorbitol dehydrogenase.

The compounds of Formula (I), the stereoisomers and prodrugs thereof, and the pharmaceutically acceptable salts of the compounds, stereoisomers, and prodrugs, can also be used in combination with sodium-hydrogen exchanger type 1 (NHE-1) inhibitors. Examples of such NHE-1 inhibitors may comprise, inter alia, those compounds disclosed in International Application Publication No. WO 99/43663.

The compounds of Formula (I), the stereoisomers and prodrugs thereof, and the pharmaceutically acceptable salts of the compounds, stereoisomers, and prodrugs, can also be used in combination with a glycogen phosphorylase inhibitor.

Any glycogen phosphorylase inhibitor may be used in combination with the compounds of Formula (I), the stereoisomers and prodrugs thereof, and the pharmaceutically acceptable salts of the compounds, stereoisomers, and prodrugs. Glycogen phosphorylase inhibition is readily determined by one skilled in the art according to standard assays (see, for example, Pesce, et al., Clinical Chemistry, 23, 1711–1717). A variety of glycogen phosphorylase inhibitors will be known to those skilled in the art (e.g., International Application Publication No. WO 95/24391 and those inhibitors disclosed in U.S. Pat. No. 5,952,363). The following publications also disclose glycogen phosphorylase inhibitors that can be used in accordance with methods of the present invention: U.S. Pat. No. 5,998,463; Oikanomakos et al., Protein Science, 8 (10), 1930–1945 (1999), which in particular discloses the compound 3-isopropyl-4-(2-chlorophenyl)-1,4-dihydro-1-ethyl-2-methylpyridine; International Application Publication Nos. WO 9524391; WO 9709040; WO 9840353; WO 9850359; and WO 9731901; European Application Publication No. EP 0 884 050; and Hoover, et al., J. Med. Chem., 41, 2934–2938 (1998).

One class of generally preferred glycogen phosphorylase inhibitors useful in such combinations comprises, for example, the compounds disclosed in U.S. Provisional Application No. 60/157,148, filed Sep. 30, 1999, and in commonly assigned International Application Publication No's. WO 96/39384 and WO 96/39385.

Moreover, the compounds of Formula (I), the stereoisomers and prodrugs thereof, and the pharmaceutically acceptable salts of the compounds, stereoisomers, and prodrugs, can be administered in combination with other pharmaceutically active agents, such as cholesterol biosynthesis inhibitors or cholesterol absorption inhibitors, especially HMG-CoA reductase inhibitors, HMG-CoA synthase inhibitors, HMG-CoA reductase or synthase gene expression inhibitors, CETP inhibitors, bile acid sequesterants, fibrates, ACAT inhibitors, squalene synthetase inhibitors, anti-oxidants, or niacin.

The compounds of Formula (I), the stereoisomers and prodrugs thereof, and the pharmaceutically acceptable salts of the compounds, stereoisomers, and prodrugs, may also be administered in combination with naturally occurring compounds that act to lower plasma cholesterol levels. Such naturally occurring compounds are commonly known as nutraceuticals and may comprise, for example, garlic extract, niacin, and the like.

In addition, the compounds of Formula (I), the stereoisomers and prodrugs thereof, and the pharmaceutically acceptable salts of the compounds, stereoisomers, and prodrugs, can be used in combination with an apolipoprotein B secretion inhibitor and/or microsomal triglyceride transfer protein (MTP) inhibitor. Some preferred apolipoprotein B secretion inhibitors and/or MTP inhibitors are disclosed in commonly assigned U.S. Pat. No. 5,919,795.

A variety of apo B secretion/MTP inhibitors will be known to one of ordinary skill in the art. Although any apo B secretion/MTP inhibitor may be used in the practice of the pharmaceutical compositions, combinations, methods, and kits of the instant invention, generally preferred apo B secretion/MTP inhibitors comprise those compounds that are disclosed in, for example, European Application Publication Nos. EP 0 643 057, EP 0 719 763, EP 0 753 517, EP 0 764 647, EP 0 765 878, EP 0 779 276, EP 0 779 279, EP 0 799 828, EP 0 799 829, EP 0 802 186, EP 0 802 188, EP 0 802 192, and EP 0 802 197; International Application Publication Nos. WO 96/13499, WO 96/33193, WO 96/40640, WO 97/26240, WO 97/43255, WO 97/43257, WO 98/16526 and WO 98/23593; and U.S. Pat. Nos. 5,595, 872; 5,646,162; 5,684,014; 5,712,279; 5,739,135 and 5,789, 197.

Especially preferred apo-B secretion/MTP inhibitors are those biphenyl-2-carboxylic acid-tetrahydroisoquinolin-6-yl amide derivatives disclosed in International Application Publication Nos. WO 96/40640 and WO 98/23593. Especially preferred apo B secretion/MTP inhibitors disclosed in International Application Publication Nos. WO 96/40640 and WO 98/23593, and useful in the pharmaceutical compositions, combinations, methods, and kits of the present invention, are 4'-trifluoromethyl-biphenyl-2-carboxylic acid-[2-(1 H-[1,2,4]triazol-3-ylmethyl)-1,2,3,4-tetrahydroisoquin-6-yl]-amide and 4'-trifluoromethyl-biphenyl-2-carboxylic acid-[2-(acetylaminoethyl)-1,2,3,4-tetrahydroisoquinolin-6-yl]-amide.

Another especially preferred class of apo B secretion/MTP inhibitors is disclosed in U.S. Pat. Nos. 5,595,872; 5,721,279; 5,739,135 and 5,789,197.

Especially preferred apo B secretion/MTP inhibitors disclosed in U.S. Pat. Nos. 5,595,872; 5,721,279; 5,739,135 and 5,789,197 and useful in the pharmaceutical compositions, combinations, methods, and kits of the present invention, are 9-(4-{4-[4'trifluoromethyl-biphenyl-2-carbonyl)-amino]-piperidin-1-yl}-butyl-9H-fluorene-9-carboxylic acid—(2,2,2-trifluoroethyl)-amide and 9-{4-[4-(2-benzothiazol-2-yl-benzoylamino)-piperidin-1-yl]-butyl}-9H-fluorene-9-carboxylic acid-(2,2,2-trifluoroethyl)-amide.

Another class of especially preferred apo B secretion/MTP inhibitors is disclosed in International Application Publication No. WO 98/16526.

Especially preferred apo B secretion/MTP inhibitors disclosed in International Application Publication No. WO 98/16526, and useful in the pharmaceutical compositions, combinations, methods, and kits of the present invention, are [11a-R]-8-[(4-cyanophenyl)methoxy]-2-cyclopentyl-7-(prop-2-enyl)-2,3,11,11a-tetrahydro-6H-pyrazino[1,2b]isoquinoline-1,4-dione and [11 a-R]-cyclopentyl-7-(prop-2-enyl)-8-[(pyridin-2-yl)methoxy]-2,3,11,11a-tetrahydro-6H-pyrazino[1,2b]isoquinoline-1,4-dione.

Another especially preferred class of apo B secretion/MTP inhibitors is disclosed in U.S. Pat. No. 5,684,014.

An especially preferred apo B secretion/MTP inhibitor disclosed in U.S. Pat. No. 5,684,014, and useful in the pharmaceutical compositions, combinations, methods, and kits of the present invention, is 2-cyclopentyl-2-[4-(2,4-dimethyl-pyrido[2,3-b]indol-9-ylmethyl)-phenyl]—N—(2-hydroxy-1-phenyl-ethyl)-acetamide.

Yet another class of especially preferred apo B secretion/MTP inhibitors is disclosed in U.S. Pat. No. 5,646,162.

An especially preferred apo B secretion/MTP inhibitor disclosed in U.S. Pat. No. 5,646,162 and useful in the pharmaceutical compositions, combinations, methods, and kits of the present invention, is 2-cyclopentyl-N-(2-hydroxy-1-phenylethyl)-2-[4-(quinolin-2-ylmethoxy)-phenyl]-acetamide.

Additional apo B secretion/MTP inhibitors that can be used in combination with the compounds of Formula (I), the stereoisomers and prodrugs thereof, and the pharmaceutically acceptable salts of the compounds, stereoisomers, and prodrugs, are disclosed in U.S. Provisional Application No. 60/164,803, filed Nov. 11, 1999. Examples of specific preferred apo B secretion/MTP inhibitors are disclosed in the aforementioned provisional application, which is incorporated herein by reference.

Specific cholesterol absorption inhibitors and cholesterol biosynthesis inhibitors are described in detail below. Additional cholesterol absorption inhibitors will be known to one of ordinary skill in the art and are described, for example, in International Application Publication No. WO 94/00480.

Any HMG-CoA reductase inhibitor may be employed as an additional compound in the combination therapy aspect of the present invention.

The term HMG-CoA reductase inhibitor refers to a compound that inhibits the biotransformation of hydroxymethylglutaryl-coenzyme A to mevalonic acid as catalyzed by the enzyme HMG-CoA reductase. Such inhibition may be determined readily by one of skill in the art according to standard assays (e.g., Methods of Enzymology, 71, 455–509 (1981), and the references cited therein). A variety of these compounds are described and referenced below. U.S. Pat. No. 4,231,938 discloses certain compounds isolated after cultivation of a microorganism belonging to the genus Aspergillus, such as lovastatin. Also, U.S. Pat. No. 4,444,784 discloses synthetic derivatives of the aforementioned compounds, such as simvastatin. Additionally, U.S. Pat. No. 4,739,073 discloses certain substituted indoles, such as fluvastatin. Further, U.S. Pat. No. 4,346,227 discloses ML-236B derivatives, such as pravastatin. Additionally, European Application Publication No. EP 0 491,226 teaches certain pyridyidihydroxyheptenoic acids, such as rivastatin. Also, U.S. Pat. No. 4,647,576 discloses certain 6-[2-(substituted-pyrrol-1-yl)-alkyl]-pyran-2-ones such as atorvastatin. Other HMG-CoA reductase inhibitors will be known to those skilled in the art. Examples of marketed products containing HMG-CoA reductase inhibitors include Baycol®, Lescol®, Lipitor®, Mevacor®, Pravachol® and Zocor®.

Any HMG-CoA synthase inhibitor may be used as an additional compound in the combination therapy aspect of this invention. The term HMG-CoA synthase inhibitor refers to a compound that inhibits the biosynthesis of hydroxymethylglutaryl-coenzyme A from acetyl-coenzyme A and acetoacetyl-coenzyme A, catalyzed by the enzyme HMG-CoA synthase. Such inhibition may be determined readily by one of skill in the art according to standard assays (e.g., Methods of Enzymology, 35, 155–160 (1975); and Methods of Enzymology, 110, 19–26 (1985); and the references cited therein). A variety of these compounds are described and referenced below. U.S. Pat. No. 5,120,729 discloses certain beta-lactam derivatives. U.S. Pat. No. 5,064,856 discloses certain spiro-lactone derivatives prepared by culturing the microorganism MF5253. U.S. Pat. No. 4,847,271 discloses certain oxetane compounds such as 11-(3-hydroxymethyl-4-oxo-2-oxetayl)-3,5,7-trimethyl-2,4-undecadienoic acid derivatives. Other HMG-CoA synthase inhibitors useful in the methods, compositions and kits of the present invention will be known to one of ordinary skill in the art.

Any compound that decreases HMG-CoA reductase gene expression may be used as an additional compound in the combination therapy aspect of this invention. These agents may be HMG-CoA reductase transcription inhibitors that block the transcription of DNA or translation inhibitors that prevent translation of mRNA coding for HMG-CoA reductase into protein. Such inhibitors may either affect transcription or translation directly, or may be biotransformed into compounds that have the aforementioned attributes by one or more enzymes in the cholesterol biosynthetic cascade or may lead to the accumulation of an isoprene metabolite that has the aforementioned activities. Such regulation is readily determined by those skilled in the art according to standard assays (Methods of Enzymology, 110, 9–19 1985). Several such compounds are described and referenced below; however, other inhibitors of HMG-CoA reductase gene expression will be known to those skilled in the art, for example, U.S. Pat. No. 5,041,432 discloses certain 15-substituted lanosterol derivatives that are inhibitors of HMG-CoA reductase gene expression. Other oxygenated sterols that suppress the biosynthesis of HMG-CoA reductase are discussed by E.I. Mercer (Prog. Lip. Res., 32, 357–416 1993).

Any compound having activity as a CETP inhibitor can serve as the second compound in the combination therapy aspect of the instant invention.

The term CETP inhibitor refers to compounds that inhibit the cholesteryl ester transfer protein (CETP) mediated transport of various cholesteryl esters and triglycerides from HDL to LDL and VLDL. A variety of these compounds are described and referenced below; however, other CETP inhibitors will be known to those skilled in the art. U.S. Pat. No. 5,512,548 discloses certain polypeptide derivatives having activity as CETP inhibitors, while certain CETP-inhibitory rosenonolactone derivatives and phosphate-containing analogs of cholesteryl ester are disclosed in J. Antibiot., 49 (8), 815–816 (1996), and Bioorg. Med. Chem. Lett., 6, 1951–1954 (1996), respectively.

Preferred CETP inhibitors that can be used in combination with the compounds of Formula (I), the stereoisomers and prodrugs thereof, and the pharmaceutically acceptable salts of the compounds, stereoisomers, and prodrugs, may comprise those compounds described in commonly assigned U.S. application Ser. No. 09/391,152, filed Sep. 7, 1999.

Any ACAT inhibitor can serve as an additional compound in the combination therapy aspect of this invention.

The term ACAT inhibitor refers to a compound that inhibits the intracellular esterification of dietary cholesterol by the enzyme acyl CoA: cholesterol acyltransferase. Such inhibition may be determined readily by one of skill in the art according to standard assays, such as the method of Heider et al. described in Journal of Lipid Research, 24, 1127 (1983). A variety of these compounds are described and referenced below; however, other ACAT inhibitors will be known to one of ordinary skill in the art. For example, U.S. Pat. No. 5,510,379 discloses certain carboxysulfonates, while International Application Publication Nos. WO 96/26948 and WO 96/10559 both disclose urea derivatives having ACAT inhibitory activity.

Any compound having activity as a squalene synthetase inhibitor can serve as an additional compound in the combination therapy aspect of the instant invention.

The term squalene synthetase inhibitor refers to compounds that inhibit the condensation of two molecules of farnesylpyrophosphate to form squalene, a reaction that is catalyzed by the enzyme squalene synthetase. Such inhibition is readily determined by those skilled in the art according to standard methodology (Methods of Enzymology, 15, 393–454 (1969); and Methods of Enzymology, 110, 359–373 (1985); and references cited therein). A summary of squalene synthetase inhibitors has been compiled in Curr. Op. Ther. Patents, 861–4, (1993). European Application Publication No. 0 567 026 A1 discloses certain 4,1-benzoxazepine derivatives as squalene synthetase inhibitors and their use in the treatment of hypercholesterolemia and as fungicides. European Application Publication No. 0 645 378 A1 discloses certain seven- or eight-membered heterocycles as squalene synthetase inhibitors and their use in the treatment and prevention hypercholesterolemia and fungal infections. European Application Publication No. 0 645 377 A1 discloses certain benzoxazepine derivatives as squalene synthetase inhibitors useful for the treatment of hypercholesterolemia or coronary sclerosis. European Application Publication No. 0 611 749 A1 discloses certain substituted amic acid derivatives useful for the treatment of arteriosclerosis. European Application Publication No. 0 705 607 A2 discloses certain condensed seven- or eight-membered heterocyclic compounds useful as antihypertriglyceridemic agents. International Application Publication WO 96/09827 discloses certain combinations of cholesterol absorption inhibitors and cholesterol biosynthesis inhibitors including benzoxazepine derivatives and benzothiazepine derivatives. European Application Publication No. 0 701 725 A1 discloses a process for preparing certain optically-active compounds, including benzoxazepine derivatives, having plasma cholesterol and triglyceride lowering activities.

Other compounds that are marketed for treating hyperlipidemia, including hypercholesterolemia, and which are intended to help prevent or treat atherosclerosis, include bile acid sequestrants, such as Colestid®, LoCholest®, and Questran®; and fibric acid derivatives, such as Atromid®, Lopid®, and Tricor®. These compounds can also be used in combination with the compounds of Formula (I), the stereoisomers and prodrugs thereof, and the pharmaceutically acceptable salts of the compounds, stereoisomers, and prodrugs.

The compounds of Formula (I), the stereoisomers and prodrugs thereof, and the pharmaceutically acceptable salts of the compounds, stereoisomers, and prodrugs, can also be administered together with a lipase inhibitor and/or a glucosidase inhibitor, which are typically used in the treatment of conditions resulting from the presence of excess triglycerides, free fatty acids, cholesterol, cholesterol esters or glucose including, inter alia, obesity, hyperlipidemia, hyperlipoproteinemia, Syndrome X, and the like.

Any lipase inhibitor or glucosidase inhibitor may be employed in combination with the compounds of Formula (I), the stereoisomers and prodrugs thereof, and the pharmaceutically acceptable salts of the compounds, stereoisomers, and prodrugs. Preferred lipase inhibitors comprise gastric or pancreatic lipase inhibitors. Generally preferred glucosidase inhibitors comprise amylase inhibitors.

A lipase inhibitor inhibits the metabolic cleavage of dietary triglycerides into free fatty acids and monoglycerides. Under normal physiological conditions, lipolysis occurs via a discreet, two-step process involving acylation of an activated serine moiety of the lipase enzyme. This leads to the production of a fatty acid-lipase hemiacetal intermediate, which is then cleaved to release a diglyceride. Following further deacylation, the lipase-fatty acid intermediate is cleaved, resulting in free lipase, a monoglyceride and a fatty acid. The resultant free fatty acids and monoglycerides are incorporated into bile acid-phospholipid micelles, which are subsequently absorbed at the level of the brush border of the small intestine. The micelles eventually enter the peripheral circulation as chylomicrons. Accordingly, compounds, including lipase inhibitors, that selectively limit or inhibit the absorption of ingested fat precursors, are useful in the treatment of conditions including obesity, hyperlipidemia, hyperlipoproteinemia, Syndrome X, and the like.

Pancreatic lipase mediates the metabolic cleavage of fatty acids from triglycerides at the 1- and 3-carbon positions. The primary site of the metabolism of ingested fats is in the duodenum and proximal jejunum by pancreatic lipase, which is usually secreted in vast excess of the amounts necessary for the breakdown of fats in the upper small intestine. Because pancreatic lipase is the primary enzyme required for the absorption of dietary triglycerides, inhibitors have utility in the treatment of obesity and the other related conditions.

Gastric lipase is an immunologically distinct lipase that is responsible for approximately 10 to 40% of the digestion of dietary fats. Gastric lipase is secreted in response to mechanical stimulation, ingestion of food, the presence of a fatty meal, or by sympathetic agents. Gastric lipolysis of ingested fats is of physiological importance in the provision of fatty acids needed to trigger pancreatic lipase activity in the intestine and is also of importance for fat absorption in a variety of physiological and pathological conditions associated with pancreatic insufficiency. See, for example, C. K. Abrams, et al., Gastroenterology, 92, 125 (1987).

A variety of lipase inhibitors will be known to one of ordinary skill in the art. However, in the practice of the pharmaceutical compositions, combinations, methods, and kits of the instant invention, generally preferred lipase inhibitors comprise those inhibitors that are selected from the group consisting of lipstatin, tetrahydrolipstatin (orlistat), FL-386, WAY-121898, Bay-N-3176, valilactone, esterastin, ebelactone A, ebelactone B and RHC 80267. The compound tetrahydrolipstatin is especially preferred.

The pancreatic lipase inhibitors lipstatin, 2S, 3S, 5S, 7Z, 10Z)-5-[(S)-2-formamido-4-methyl-valeryloxy]-2-hexyl-3-hydroxy-7,10-hexadecanoic acid lactone, and tetrahydrolipstatin (orlistat), 2S, 3S, 5S)-5-[(S)-2-formamido-4-methyl-valeryloxy]-2-hexyl-3-hydroxy-hexadecanoic acid lactone, and the variously substituted N-formylleucine derivatives and stereoisomers thereof, are disclosed in U.S. Pat. No. 4,598,089.

The pancreatic lipase inhibitor FL-386, 1-[4-(2-methylpropyl)cyclohexyl]-2-[(phenylsulfonyl)oxy]-ethanone, and the variously substituted sulfonate derivatives related thereto, are disclosed in U.S. Pat. No. 4,452,813.

The pancreatic lipase inhibitor WAY-121898, 4-phenoxyphenyl-4-methylpiperidin-1-yl-carboxylate, and the various carbamate esters and pharmaceutically acceptable salts related thereto, are disclosed in U.S. Pat. Nos. 5,512,565; 5,391,571 and 5,602,151.

The lipase inhibitor Bay-N-3176, N-3-trifluoromethylphenyl—N'-3-chloro-4'-trifluoromethylphenylurea, and the various urea derivatives related thereto, are disclosed in U.S. Pat. No. 4,405,644.

The pancreatic lipase inhibitor valilactone, and a process for the preparation thereof by the microbial cultivation of Actinomycetes strain MG147-CF2, are disclosed in Kitahara, et al., J. Antibiotics, 40 (11), 1647–1650 (1987).

The lipase inhibitor esteracin, and certain processes for the preparation thereof by the microbial cultivation of Streptomyces strain ATCC 31336, are disclosed in U.S. Pat. Nos. 4,189,438 and 4,242,453.

The pancreatic lipase inhibitors ebelactone A and ebelactone B, and a process for the preparation thereof by the microbial cultivation of Actinomycetes strain MG7-G1, are disclosed in Umezawa, et al., J. Antibiotics, 33, 1594–1596 (1980). The use of ebelactones A and B in the suppression of monoglyceride formation is disclosed in Japanese Kokai 08-143457, published Jun. 4, 1996.

The lipase inhibitor RHC 80267, cyclo—O,O'-[(1,6-hexanediyl)-bis-(iminocarbonyl)]dioxime, and the various bis(iminocarbonyl)dioximes related thereto may be prepared as described in Petersen et al., Liebig's Annalen, 562, 205–229 (1949). The ability of RHC 80267 to inhibit the activity of myocardial lipoprotein lipase is disclosed in Carroll et al., Lipids, 27, pp. 305–307 (1992) and Chuang et al., J. Mol. Cell Cardiol., 22, 1009–1016 (1990).

Any suitable dosage of a lipase inhibitor is used in aspects of the present invention comprising such inhibitors. The dosage of the lipase inhibitor is generally in the range of from about 0.01 to about 50 mg/kg body weight of the subject per day, preferably from about 0.05 to about 10 mg/kg body weight of the subject per day, administered singly or as a divided dose. For example, where the lipase inhibitor is tetrahydrolipstatin, the dosage of tetrahydrolipstatin is preferably from about 0.05 to 2 mg/kg body weight of the subject per day. In practice, the physician will determine the actual dosage of the lipase inhibitor which will be most suitable for an individual patient and it will vary with, e.g., age, weight and response of the particular patient. The above dosages of lipase inhibitors are exemplary, but there can be, of course, individual instances where higher or lower dosage ranges of such lipase inhibitors are merited, and all such dosages are intended to be within the scope of the present invention.

A glucosidase inhibitor inhibits the enzymatic hydrolysis of complex carbohydrates by glycoside hydrolases, for example amylase or maltase, into bioavailable simple sugars, for example, glucose. The rapid metabolic action of glucosidases, particularly following the intake of high levels of carbohydrates, results in a state of alimentary hyperglycemia which, in adipose or diabetic subjects, leads to enhanced secretion of insulin, increased fat synthesis and a reduction in fat degradation. Following such hyperglycemias, hypoglycemia frequently occurs, due to the augmented levels of insulin present. Additionally, it is known that both hypoglycemias and chyme remaining in the stomach promotes the production of gastric juice, which initiates or favors the development of gastritis or duodenal ulcers. Accordingly, glucosidase inhibitors are known to have utility in accelerating the passage of carbohydrates through the stomach and inhibiting the absorption of glucose from the intestine. Furthermore, the conversion of carbohydrates into lipids of the fatty tissue and the subsequent incorporation of alimentary fat into fatty tissue deposits is accordingly reduced or delayed, with the concomitant benefit of reducing or preventing the deleterious abnormalities resulting therefrom.

Any glucosidase inhibitor may be employed in combination with the compounds of Formula (I), the stereoisomers and prodrugs thereof, and the pharmaceutically acceptable salts of the compounds, stereoisomers, and prodrugs, however, generally preferred glucosidase inhibitors comprise amylase inhibitors. An amylase inhibitor is a glucosidase inhibitor that inhibits the enzymatic degradation of starch or glycogen into maltose. The inhibition of such enzymatic degradation is beneficial in reducing amounts of bioavailable sugars, including glucose and maltose, and the concomitant deleterious conditions resulting therefrom.

A variety of glucosidase and amylase inhibitors will be known to one of ordinary skill in the art. However, in the practice of the pharmaceutical compositions, combinations, methods, and kits of the instant invention, generally preferred glucosidase inhibitors are those inhibitors selected from the group consisting of acarbose, adiposine, voglibose, miglitol, emiglitate, MDL-25637, camiglibose, tendamistate, Al-3688, trestatin, pradimicin-Q and salbostatin.

The glucosidase inhibitor acarbose, O-4,6-dideoxy-4-[[(1S,4R,5S,6S)-4,5,6-trihydroxy-3-(hydroxymethyl)-2-cyclohexen-1-yl]amino]-α-glucopyranosyl-(1→4)-O-α-D-glucopyranosyl-(1→4)-D-glucose, the various amino sugar derivatives related thereto and a process for the preparation thereof by the microbial cultivation of Actinoplanes strains SE 50 (CBS 961.70), SB 18 (CBS 957.70), SE 82 (CBS 615.71), SE 50/13 (614.71) and SE 50/110 (674.73) are disclosed in U.S. Pat. Nos. 4,062,950 and 4,174,439 respectively.

The glucosidase inhibitor adiposine, consisting of adiposine forms 1 and 2, is disclosed in U.S. Pat. No. 4,254,256. Additionally, a process for the preparation and purification of adiposine is disclosed in Namiki et al., J. Antiobiotics, 35, 1234–1236 (1982).

The glucosidase inhibitor voglibose, 3,4-dideoxy-4-[[2-hydroxy-1-(hydroxymethyl)ethyl]amino]-2-C-(hydroxymethyl)-D-epi-inositol, and the various N-substituted pseudo-aminosugars related thereto, are disclosed in U.S. Pat. No. 4,701,559.

The glucosidase inhibitor miglitol, (2R,3R,4R,5S)-1-(2-hydroxyethyl)-2-(hydroxymethyl)-3,4,5-piperidinetriol, and the various 3,4,5-trihydroxypiperidines related thereto, are disclosed in U.S. Pat. No. 4,639,436.

The glucosidase inhibitor emiglitate, ethyl p-[2-[(2R,3R,4R,5S)-3,4,5-trihydroxy-2-(hydroxymethyl)piperidino] ethoxy]-benzoate, the various derivatives related thereto and pharmaceutically acceptable acid addition salts thereof, are disclosed in U.S. Pat. No. 5,192,772.

The glucosidase inhibitor MDL-25637, 2,6-dideoxy-7-O-β-D-glucopyrano-syl-2,6-imino-D-glycero-L-gluco-heptitol, the various homodisaccharides related thereto and the pharmaceutically acceptable acid addition salts thereof, are disclosed in U.S. Pat. No. 4,634,765.

The glucosidase inhibitor camiglibose, methyl 6-deoxy-6-[(2R,3R,4R,5S)-3,4,5-trihydroxy-2-(hydroxymethyl) piperidino]-α-D-glucopyranoside sesquihydrate, the deoxynojirimycin derivatives related thereto, the various pharmaceutically acceptable salts thereof and synthetic methods for the preparation thereof, are disclosed in U.S. Pat. Nos. 5,157,116 and 5,504,078.

The amylase inhibitor tendamistat, the various cyclic peptides related thereto and processes for the preparation thereof by the microbial cultivation of Streptomyces tendae strains 4158 or HAG 1226, are disclosed in U.S. Pat. No. 4,451,455.

The amylase inhibitor Al-3688, the various cyclic polypeptides related thereto, and a process for the preparation thereof by the microbial cultivation of Streptomyces aureofaciens strain FH 1656, are disclosed in U.S. Pat. No. 4,623,714.

The amylase inhibitor trestatin, consisting of a mixture of trestatin A, trestatin B and trestatin C, the various trehalose-containing aminosugars related thereto and a process for the preparation thereof by the microbial cultivation of Streptomyces dimorphogenes strains NR-320—OM7HB and NR-320—OM7HBS, are disclosed in U.S. Pat. No. 4,273,765.

The glucosidase inhibitor pradimicin-Q and a process for the preparation thereof by the microbial cultivation of Actinomadura verrucospora strains R103–3 or A10102, are disclosed in U.S. Pat. Nos. 5,091,418 and 5,217,877 respectively.

The glycosidase inhibitor salbostatin, the various pseudosaccharides related thereto, the various pharmaceutically acceptable salts thereof and a process for the preparation thereof by the microbial cultivation of Streptomyces albus strain ATCC 21838, are disclosed in U.S. Pat. No. 5,091,524.

Preferred lipase inhibitors comprise compounds selected from the group consisting of lipstatin, tetrahydrolipstatin, FL-386, WAY-121898, Bay-n-3176, valilactone, esteracin, ebelactone A, ebelactone B, RHC 80267, stereoisomers thereof, and pharmaceutically acceptable salts of said compounds and stereoisomers. The compound tetrahydrolipstatin is especially preferred.

Preferred glucosidase inhibitors comprise compounds selected from the group consisting of acarbose, adiposine, voglibose, miglitol, emiglitate, MDL-25637, camiglibose, pradimicin-Q, and salbostatin. An especially preferred glucosidase inhibitor is acarbose. Especially preferred glucosidase inhibitors further comprise amylase inhibitors that are selected from the group consisting of tendamistate, Al-3688 and trestatin.

In another aspect of the invention, the compounds of Formula (I), the stereoisomers and prodrugs thereof, and the pharmaceutically acceptable salts of the compounds, stereoisomers, and prodrugs, can be used in combination with an anti-obesity agent.

The anti-obesity agent is preferably selected from the group consisting of a $\beta_3$-adrenergic receptor agonist, a cholecystokinin-A agonist, a monoamine reuptake inhibitor, a sympathomimetic agent, a serotoninergic agent, a dopamine agonist, a melanocyte-stimulating hormone receptor agonist or mimetic, a melanocyte-stimulating hormone receptor analog, a cannabinoid receptor antagonist, a melanin concentrating hormone antagonist, leptin, a leptin analog, a leptin receptor agonist, a galanin antagonist, a lipase inhibitor, a bombesin agonist, a neuropeptide-Y antagonist, a thyromimetic agent, dehydroepiandrosterone or an analog thereof, a glucocorticoid receptor agonist or antagonist, an orexin receptor antagonist, a urocortin binding protein antagonist, a glucagon-like peptide-1 receptor agonist, and a ciliary neurotrophic factor.

Especially preferred anti-obesity agents comprise those compounds selected from the group consisting of sibutramine, fenfluramine, dexfenfluramine, bromocriptine, phentermine, ephedrine, leptin, phenylpropanolamine pseudoephedrine, {4-[2-(2-[6-aminopyridin-3-yl]-2(R)-hydroxyethylamino)ethoxy]phenyl}acetic acid, {4-[2-(2-[6-aminopyridin-3-yl]-2(R)-hydroxyethylamino)ethoxy] phenyl}benzoic acid, {4-[2-(2-[6-aminopyridin-3-yl]-2(R)-hydroxyethylamino)ethoxy]phenyl}propionic acid, and {4-[2-(2-[6-aminopyridin-3-yl]-2(R)-hydroxyethylamino) ethoxy]phenoxy}acetic acid.

Suitable anorectic agents for the compositions, methods and kits of the present invention can be prepared using methods known to those skilled in the art, for example, phentermine can be prepared as described in U.S. Pat. No. 2,408,345; sibutramine can be prepared as described in U.S. Pat. No. 4,929,629; fenfluramine and dexfenfluramine can be prepared as described in U.S. Pat. No. 3,198,834; and bromocriptine can be prepared as described in U.S. Pat. Nos. 3,752,814 and 3,752,888.

Any suitable dosage of an anorectic agent can be used in aspects of the present invention comprising such agents. The dosage of the anorectic agent is generally in the range of from about 0.01 to about 50 mg/kg body weight of the subject per day, preferably from about 0.1 to about 10 mg/kg body weight of the subject per day, administered singly or as a divided dose. For example, where the anorectic agent is phentermine, the dosage of phentermine is from about 0.01 to 50 mg/kg body weight of the subject per day, preferably from about 0.1 to about 1 mg/kg body weight of the subject per day. In addition, where the anorectic agent is sibutramine, the dosage range is from about 0.01 to about 50 mg/kg body weight of the subject per day, preferably from about 0.1 to about 1 mg/kg body weight of the subject per day; where the anorectic agent is dexfenfluramine or fenfluramine, the dosage range is from about 0.01 to about 50 mg/kg body weight of the subject per day, preferably from about 0.1 to about 1 mg/kg body weight of the subject per day; and where the anorectic agent is bromocriptine, the dosage range is from about 0.01 to about 10 mg/kg body weight of the subject per day, preferably from about 0.1 to about 1 mg/kg body weight of the subject per day. In practice, the physician will determine the actual dosage of the anorectic agent which will be most suitable for an individual patient and it will vary with, e.g., age, weight and response of the particular patient. The above dosages of anorectic agents are exemplary, but there can be, of course, individual instances where higher or lower dosage ranges of such anorectic agents are merited, and all such dosages are within the scope of the present invention.

The compounds of Formula (I), the stereoisomers and prodrugs thereof, and the pharmaceutically acceptable salts of the compounds, stereoisomers, and prodrugs, can also be used in combination with an antihypertensive agent.

Examples of presently marketed products containing antihypertensive agents include calcium channel blockers, such as Cardizem®, Adalat®, Calan®, Cardene®, Covera®, Dilacor®, DynaCirc®, Procardia XL®, Sular®, Tiazac®, Vascor®, Verelan®, Isoptin®, Nimotop®, Norvasc®, and Plendil®; angiotensin converting enzyme (ACE) inhibitors, such as Accupril®, Altace®, Captopril®, Lotensin®, Mavik®, Monopril®, Prinivil®, Univasc®, Vasotec® and Zestril®. In addition, diuretics and combinations of the above antihypertensive agents have been employed and are contemplated to be used in combination with the compounds of Formula (I), the stereoisomers and prodrugs thereof, and the pharmaceutically acceptable salts of the compounds, stereoisomers, and prodrugs.

The compounds of Formula (I), the stereoisomers and prodrugs thereof, and the pharmaceutically acceptable salts of the compounds, stereoisomers, and prodrugs, can also be used in combination with an antidepressant.

Examples of marketed antidepressants that can be used in combination with a compound of the present invention include monoamine oxidase inhibitors such as Nardil® and Parnate®; selective serotonin reuptake inhibitors, such as Paxil®, Prozac®, and Zoloft®; triclyclics, such as Asendin®, Elavil®, Etrafon®, Limbitrol®, Norpramin®, Pamelor®, Sinequan®, Surmontil®, Tofranil®, Triavil®, and Vivactil®. Additional depressants that are useful in combination with the compounds of Formula (I), the stereoisomers and prodrugs thereof, and the pharmaceutically acceptable salts of the compounds, stereoisomers, and prodrugs, may comprise Desyrel®, Effexor®, Remeron®, Serzone®, and Wellbutrin®.

The compounds of Formula (I), the stereoisomers and prodrugs thereof, and the pharmaceutically acceptable salts of the compounds, stereoisomers, and prodrugs, can also be used in combination with a compound useful in the treatment of osteoporosis.

Examples of marketed products containing active agents useful in the treatment of osteoporosis and that can be used in combination with a compound of the present invention include biphosphonates such as Fosamax® and hormonal agents such as calcitonin and estrogens. In addition, Evista® may be used in combination with the compounds of Formula (I), the stereoisomers and prodrugs thereof, and the pharmaceutically acceptable salts of the compounds, stereoisomers, and prodrugs.

The compounds of Formula (I), the stereoisomers and prodrugs thereof, and the pharmaceutically acceptable salts of the compounds, stereoisomers, and prodrugs, are administered to a patient in need of teatment therewith in therapeutically effective amounts. The compounds can be administered alone or, preferably, as part of a pharmaceutically acceptable composition. In addition, the compounds or compositions can be administered all at once, as for example, by a bolus injection, multiple times, such as by a series of tablets, or delivered substantially uniformly over a period of time, as for example, using transdermal delivery. It is also noted that the dose of the compound can be varied over time.

In addition, the compounds of Formula (I), the stereoisomers and prodrugs thereof, and the pharmaceutically acceptable salts of the compounds, stereoisomers, and prodrugs, can be administered alone, in combination with other compounds of the present invention, or with other pharmaceutically active compounds. The other pharmaceutically active compounds can be intended to treat the same disease or condition as the compounds of the present invention or a different disease or condition. If the patient is to receive or is receiving multiple pharmaceutically active compounds, the compounds can be administered simultaneously, or sequentially in any order. For example, in the case of tablets, the active compounds may be found in one tablet or in separate tablets, which can be administered at once or sequentially. In addition, it should be recognized that the compositions may comprise different forms. For example, one or more compounds may be delivered via a tablet, while another is administered via injection or orally as a syrup. All combinations, delivery methods and administration sequences are intended to be embraced within the scope of the invention.

Since one aspect of the present invention comprises the treatment of the disease/conditions with a combination of pharmaceutically active agents that may be administered separately, the invention further relates to combining separate pharmaceutical compositions in kit form.

The kit, according to the invention, comprises two separate pharmaceutical compositions: a compound of Formula (I), or a stereoisomer or prodrug thereof, or a pharmaceutically acceptable salt of the compound, stereoisomer, or prodrug; and an additional pharmaceutically active compound. The kit further comprises a container for containing the separate compositions, such as a divided bottle or a divided foil packet. Additional examples of containers include syringes, boxes, bags, and the like. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

One well known example of such a kit is a so-called blister pack. Blister packs are well known in the packaging industry and are being widely employed for the packaging of pharmaceutical unit dosage forms (tablets, capsules, and the like).

Blister packs generally comprise a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen that the tablets or capsules so specified should be ingested. Another example of such a memory aid is a calendar printed on the card, e.g., as follows "First Week, Monday, Tuesday, . . . etc . . . Second Week, Monday, Tuesday, . . ." etc. Other variations of memory aids will be readily apparent. A "daily dose" can be a single tablet or capsule or several pills or capsules to be taken on a given day. Also, a daily dose of compounds of the present invention can consist of one tablet or capsule, while a daily dose of the second compound can consist of several tablets or capsules and vice versa. The memory aid should reflect this and aid in correct administration of the active agents.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compounds of Formula (I), the stereoisomers and prodrugs thereof, and the pharmaceutically acceptable salts of the compounds, stereoisomers, and prodrugs, and other pharmaceutically active agents, if desired, can be administered to a patient either orally, rectally, parenterally, (for example, intravenously, intramuscularly, or subcutaneously) intracistemally, intravaginally, intraperitoneally, intravesically, locally (for example, powders, ointments or drops), or as a buccal or nasal spray.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Prevention of microorganism contamination of the compositions can be accomplished with various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and gelatin.

Solid dosage forms for oral administration include capsules, tablets, powders, and granules. In such solid dosage forms, the active compound is admixed with at least one inert customary pharmaceutical excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (e) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and/or (i) lubricants, as for example, talc, calcium stearate, magnesium stearate, solid polyethylene glycols, sodium lauryl sulfate, or mixtures thereof. In the case of capsules and tablets, the dosage forms may also comprise buffering agents.

Solid compositions of a similar type may also be used as fillers in soft or hard filled gelatin capsules using such excipients as lactose or milk sugar, as well as high molecular weight polyethylene glycols, and the like.

Solid dosage forms such as tablets, dragees, capsules, and granules can be prepared with coatings and shells, such as enteric coatings and others well known in the art. They may also contain opacifying agents, and can also be of such composition that they release the active compound or compounds in a delayed manner. Examples of embedding compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

Suspensions, in addition to the active compound, may further comprise suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal or vaginal administration preferably comprise suppositories, which can be prepared by mixing a compound of the present invention with suitable non-irritating excipients or carriers such as cocoa butter, polyethylene glycol or a suppository wax, which are solid at ordinary room temperature, but liquid at body temperature, and therefore, melt in the rectum or vaginal cavity thereby releasing the active component.

Dosage forms for topical administration of the compounds of Formula (I), the stereoisomers and prodrugs thereof, and the pharmaceutically acceptable salts of the compounds, stereoisomers, and prodrugs, may comprise ointments, powders, sprays and inhalants. The active agent or agents are admixed under sterile condition with a physiologically acceptable carrier, and any preservatives, buffers, or propellants that may be required. Opthalmic formulations, eye ointments, powders, and solutions are also intended to be within the scope of the present invention.

The compounds of Formula (I), the stereoisomers and prodrugs thereof, and the pharmaceutically acceptable salts of the compounds, stereoisomers, and prodrugs, can be administered to a patient at dosage levels in the range of from about 0.7 to about 7,000 mg per day. For a normal adult human having a body weight of about 70 kg, a dosage in the range of from about 0.01 to about 100 mg per kilogram body weight is typically sufficient. The specific dosage and dosage range that can be used depends on a number of factors, including the requirements of the patient, the severity of the condition or disease being treated, and the pharmacological activity of the compound being administered. The determination of dosage ranges and optimal dosages for a particular patient is well within the ability of one of ordinary skill in the art having the benefit of the instant disclosure. It is also noted that the compounds of the present invention can be used in sustained release, controlled release, and delayed release formulations, which forms are also well known to one of ordinary skill in the art.

The following paragraphs describe exemplary formulations, dosages, etc. useful for non-human animals. The administration of the compounds of Formula (I), the stereoisomers and prodrugs thereof, and the pharmaceutically acceptable salts of the compounds, stereoisomers, and prodrugs, can be effected orally or non-orally, for example, by injection.

An amount of a compound of Formula (I), or a stereoisomer or prodrug thereof, or a pharmaceutically acceptable salt of the compound, stereoisomer, or prodrug, is administered such that an effective dose is received, generally a daily dose which, when administered orally to an animal is usually between about 0.01 and about 100 mg/kg of body weight, preferably between about 0.1 and about 50 mg/kg of body weight.

Conveniently, the compound can be carried in the drinking water so that a therapeutic dosage of the compound is ingested with the daily water supply. The compound can be directly metered into drinking water, preferably in the form of a liquid, water-soluble concentrate (such as an aqueous solution of a water-soluble salt).

Conveniently, the compound can also be added directly to the feed, as such, or in the form of an animal feed supplement, also referred to as a premix or concentrate. A premix or concentrate of the compound in a carrier is more commonly employed for the inclusion of the agent in the feed. Suitable carriers are liquid or solid, as desired, such as water, various meals such as alfalfa meal, soybean meal, cottonseed oil meal, linseed oil meal, corncob meal and corn meal, molasses, urea, bone meal, and mineral mixes such as are commonly employed in poultry feeds. A particularly effective carrier is the respective animal feed itself; that is, a small portion of such feed. The carrier facilitates uniform distribution of the compound in the finished feed with which the premix is blended. It is important that the compound be thoroughly blended into the premix and, subsequently, the feed. In this respect, the compound may be dispersed or dissolved in a suitable oily vehicle such as soybean oil, corn oil, cottonseed oil, and the like, or in a volatile organic solvent and then blended with the carrier. It will be appreciated that the proportions of compound in the concentrate are capable of wide variation since the amount of active compound in the finished feed may be adjusted by blending the appropriate proportion of premix with the feed to obtain a desired level of compound.

High potency concentrates may be blended by the feed manufacturer with proteinaceous carrier such as soybean oil meal and other meals, as described above, to produce concentrated supplements, which are suitable for direct feeding to animals. In such instances, the animals are permitted to consume the usual diet. Alternatively, such concentrated supplements may be added directly to the feed to produce a nutritionally balanced, finished feed containing a therapeutically effective level of a compound of the present invention. The mixtures are thoroughly blended by standard procedures, such as in a twin shell blender, to ensure homogeneity.

If the supplement is used as a top dressing for the feed, it likewise helps to ensure uniformity of distribution of the compound across the top of the dressed feed.

Preferred medicated swine, cattle, sheep and goat feeds generally contain from about 1 to about 400 grams of a compound of the present invention per ton of feed, the optimum amount for these animals usually being about 50 to about 300 grams per ton of feed.

Preferred poultry and domestic pet feeds usually contain about 1 to about 400 grams and preferably about 10 to about 400 grams of a compound of Formula (I), or a stereoisomer or prodrug thereof, or a pharmaceutically acceptable salt of the compound, stereoisomer, or prodrug, per ton of feed.

For parenteral administration in animals, the compounds of Formula (I), the stereoisomers and prodrugs thereof, and the pharmaceutically acceptable salts of the compounds, stereoisomers, and prodrugs, may be prepared in the form of a paste or a pellet and administered as an implant, usually under the skin of the head or ear of the animal.

In general, parenteral administration of the pharmaceutical compositions involves injection of a sufficient amount of a compound of Formula (I), or a stereoisomer or prodrug thereof, or a pharmaceutically acceptable salt of the compound, stereoisomer, or prodrug, to provide the animal with about 0.01 to about 100 mg/kg of body weight per day of the active ingredient. The preferred dosage for poultry, swine, cattle, sheep, goats and domestic pets is in the range of from about 0.1 to about 50 mg/kg/day.

Paste formulations can be prepared by dispersing a compound of the present invention in pharmaceutically acceptable oil such as peanut oil, sesame oil, corn oil or the like.

Pellets containing effective amounts of the compounds of Formula (I), the stereoisomers and prodrugs thereof, and the pharmaceutically acceptable salts of the compounds, stereoisomers, and prodrugs, can be prepared by admixing a compound of the present invention with a diluent such as carbowax, carnauba wax, and the like, and a lubricant, such as magnesium or calcium stearate, can be added to improve the pelleting process.

It is, of course, recognized that more than one pellet may be administered to an animal to achieve the desired dose level. Moreover, it has also been found that implants may also be made periodically during the animal treatment period in order to maintain the proper active agent level in the animal's body.

The terms pharmaceutically acceptable salts, esters, amides, or prodrugs mean the carboxylate salts, amino acid addition salts, esters, amides, and prodrugs of a compound that are, within the scope of sound medical judgment, suitable for use with patients without undue toxicity, irritation, allergic response, and the like, commensurate with a reasonable benefit/risk ratio, and effective for their intended use, as well as the zwitterionic forms, where possible.

The term "salts" refers to inorganic and organic salts of a compound of Formula (I), or a stereoisomer or prodrug thereof. These salts can be prepared in situ during the final isolation and purification of a compound, or by separately reacting a compound Formula (I), or a stereoisomer or prodrug thereof with a suitable organic or inorganic acid and isolating the salt thus formed. Representative salts include the hydrobromide, hydrochloride, sulfate, bisulfate, nitrate, acetate, oxalate, besylate, palmitiate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, Berge, et al., J. Pharm. Sci., 66, 1–19 (1977).

The term "prodrug" means a compound that is transformed in vivo to yield a compound of Formula (I), a stereoisomer thereof, or a pharmaceutically acceptable salt of the compound or stereoisomer. The transformation may occur by various mechanisms, such as through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I), a stereoisomer thereof, or a pharmaceutically acceptable salt of the compound or stereoisomer, contains a carboxylic acid functional group, a prodrug can comprise an ester formed by the replacement of the hydrogen atom of the acid group with a group such as $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di $(C_1-C_2)$alkylcarbamoyl-$(C_1-C_2)$alkyl and piperidino-, pyrrolidino- or morpholino$(C_2-C_3)$alkyl.

Similarly, if a compound of Formula (I), or a stereoisomer thereof, comprises an alcohol functional group, a prodrug can be formed by the replacement of the hydrogen atom of the alcohol group with a group such as $(C_1-C_6)$ alkanoyloxymethyl, 1-(($C_1-C_6$)alkanoyloxy)ethyl, 1-methyl-1-(($C_1-C_6$)alkanoyloxy)ethyl, $(C_1-C_6)$ alkoxycarbonyloxymethyl, N—$(C_1-C_6)$ alkoxycarbonylaminomethyl, succinoyl, $(C_1-C_6)$alkanoyl, α-amino$(C_1-C_4)$alkanoyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)alkyl)_2$ or glycosyl (the radical resulting from the removal of a hydroxyl group of the hemiacetal form of a carbohydrate).

If a compound of Formula (I), or a stereoisomer thereof, incorporates an amine functional group, a prodrug can be formed by the replacement of a hydrogen atom in the amine group with a group such as R-carbonyl, RO-carbonyl, NRR'-carbonyl where R and R' are each independently $(C_1-C_{10})$ alkyl, $(C_3-C_7)$cycloalkyl, benzyl, or R-carbonyl is a natural α-aminoacyl or natural α-aminoacyl-natural α-aminoacyl, —C(OH)C(O)OY wherein Y is H, $(C_1-C_6)$alkyl or benzyl, —C(OY$_0$)Y$_1$ wherein Y$_0$ is $(C_1-C_4)$ alkyl and Y$_1$ is $((C_1-C_6)$alkyl, carboxy$(C_1-C_6)$alkyl, amino$(C_1-C_4)$alkyl or mono-N- or di-N,N—$(C_1-C_6)$alkylaminoalkyl, —C(Y$_2$)Y$_3$ wherein Y$_2$ is H or methyl and Y$_3$ is mono-N- or di-N,N—$(C_1-C_6)$alkylamino, morpholino, piperidin-1-yl or pyrrolidin-1-yl.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond, both the cis- and trans- forms, as well as mixtures, are embraced within the scope of the invention.

Diasteromeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diasteromeric mixture by reaction with an appropriate optically active compound (e.g., alcohol), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention.

The compounds of Formula (I) may exist in unsolvated as well as solvated forms with pharmaceutically acceptable solvents such as water, ethanol, and the like, and it is intended that the invention embrace both solvated and unsolvated forms.

It is also possible that the compounds of Formula (I) may exist in different tautomeric forms, and all such forms are embraced within the scope of the invention. For example, all of the tautomeric forms of the imidazole moiety are included in the invention. Also, for example, all keto-enol or imine-enamine forms of the compounds are included in the invention.

One of ordinary skill in the art will recognize that the compound names pertaining to the compounds of Formula (I) disclosed herein may be based on a particular tautomer of a compound. While the name for only a particular tautomer may be used, it is intended that all tautomers are encompassed by the name of the particular tautomer and all tautomers are considered part of the present invention.

It is also intended that the invention disclosed herein encompass compounds of Formula (I) that may be synthesized in vitro using laboratory techniques, such as those well known to the synthetic organic chemist of ordinary skill, or synthesized using in vivo techniques, such as through metabolism, fermentation, digestion, and the like. It is also intended that the compounds of Formula (I) may be synthesized using a combination of in vitro and in vivo techniques.

The present invention also embraces isotopically-labelled compounds of Formula (I), which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. The compounds of Formula (I), the stereoisomers and prodrugs thereof, and the pharmaceutically acceptable salts of the compounds, stereoisomers, or prodrugs which contain the aforementioned isotopes and/or other isotopes of other atoms are intended to be within the scope of this invention.

Certain isotopically-labelled compounds of Formula (I), for example those into which radioactive isotopes such as $^3$H and $^{14}$C are incorporated, are useful in compound and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, may afford certain therapeutic advantages resulting from greater metabolic stability, for example increased in vivo half-life or reduced dosage requirements and, hence, may be preferred in some circumstances. Isotopically labelled compounds of Formula (I) can generally be prepared by carrying out the procedures analogous to those disclosed in the Schemes and/or in the Examples below, by substituting a readily available isotopically labelled reagent for a non-isotopically labelled reagent.

The compounds of structural Formula (I) may generally be prepared according to the synthetic methodologies set forth hereinbelow in Schemes 1 through 5.

Scheme 1

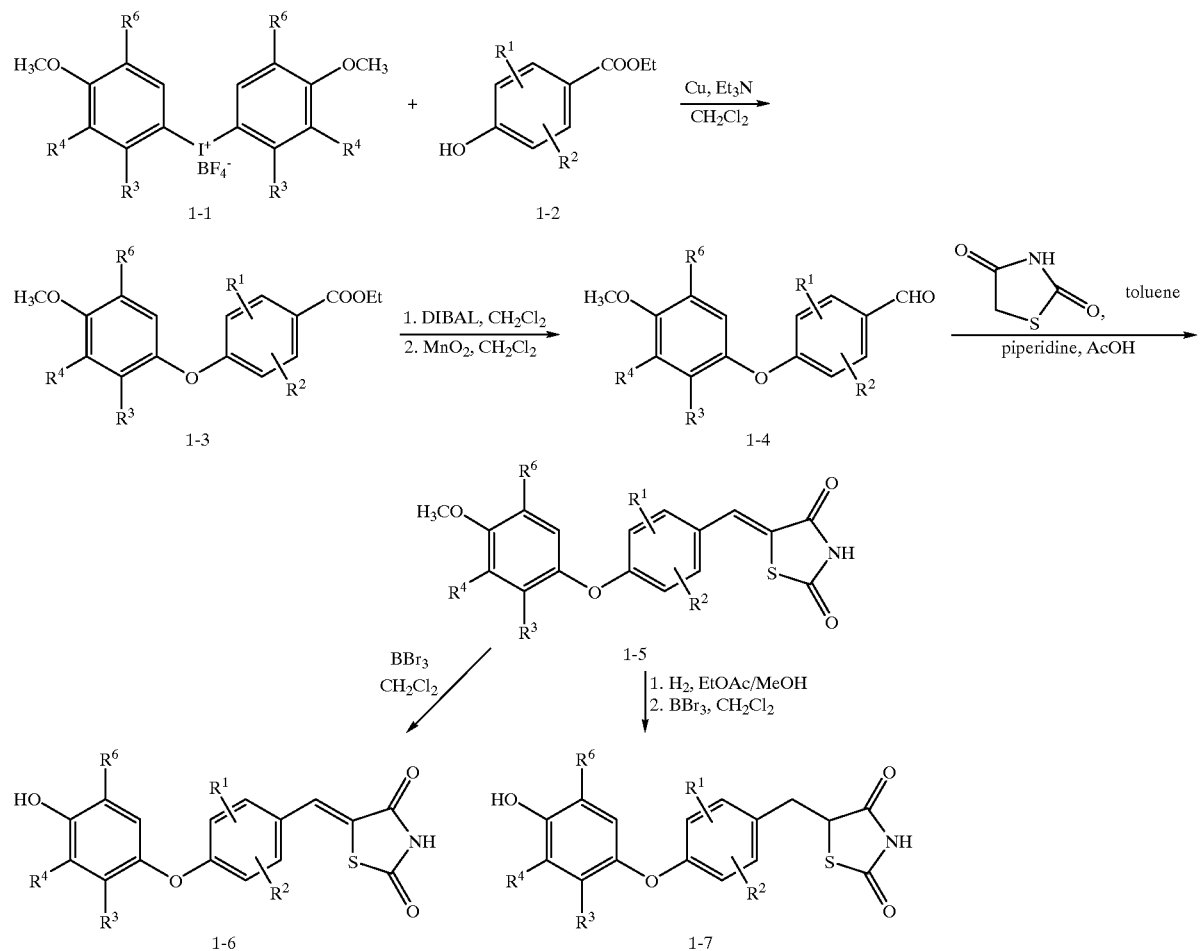

Preparation of thiazolidinedione derivatives 1-6 and 1-7 is illustrated in Scheme 1. The key intermediate diaryl ether 1-3 can be synthesized by coupling bis-aryl iodonium tetrafluoroborate 1-1 with p-hydroxybenzoate 1-2 at room temperature in a suitable organic solvent such as dichloromethane, in the presence of a copper catalyst and an appropriate base, for example, triethylamine (TEA). The preparation of the bis-aryl iodonium tetrafluoroborate 1-1 can be effected from the corresponding known anisole derivative according to the procedure disclosed in J. Med. Chem., 38, 695–707 (1995). Reduction of ester 1-3 to benzaldehyde 1-4 can be accomplished according to methods that will be well known to one of ordinary skill in the art. For example, ester 1-3 can be reduced to the corresponding alcohol by reaction with an appropriate reducing agent, for example, diisobutylaluminum hydride (DIBAL), followed by oxidation to aldehyde 1-4 by manganese dioxide. The aldehyde reaction product so produced may then be reacted via a Knoevengel condensation with thiazolidinedione in the presence of a catalytic amount of piperidinium acetate to afford benzylidene thiazolidinedione 1-5. Demethylation of the condensation product 1-5 with boron tribromide gives phenol 1-6. Hydrogenation of 1-5 gives the saturated benzyl thiazolidinedione which reacts with boron tribromide to furnish phenol 1-7.

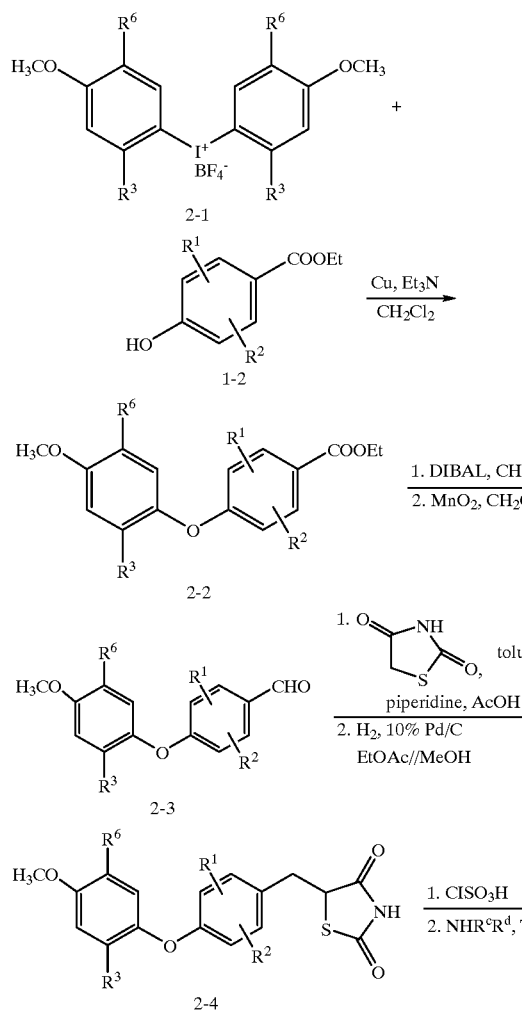

Scheme 2

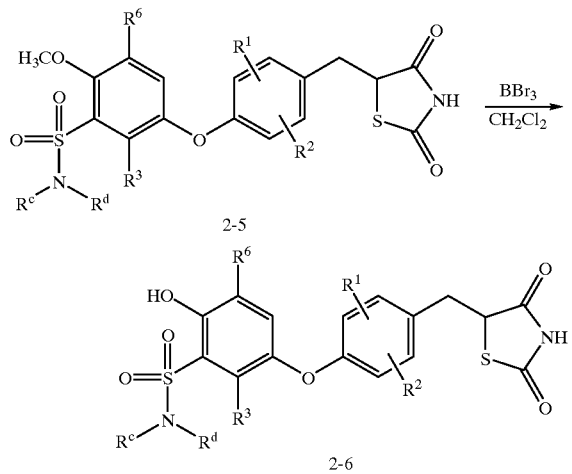

The sulfonamide derivatives 2-5 and 2-6 are prepared as depicted in Scheme 2. The bis-aryl iodonium tetrafluoroborate 2-1 is coupled with 4-hydroxybenzoate 1-2 at room temperature in dichloromethane in the presence of copper bronze and a suitable base such as triethylamine (TEA) to afford diaryl ether 2-2. Reduction of ether 2-2 with DIBAL furnishes the corresponding alcohol which is oxidized to benzaldehyde 2-3 with manganese dioxide. Condensation of aldehyde 2-3 with thiazolidinedione produces an intermediate benzylidene thiazolidinedione which is hydrogenated to furnish benzyl thiazolidinedione 2-4. A subsequent chlorosulfonylation reaction yields a 3'-sulfonyl chloride which is then reacted with a primary or secondary amine to afford 3'-sulfonylamide 2-5. Demethylation of 2-5 with boron tribromide gives hydroxysulfonamide 2-6.

Scheme 3

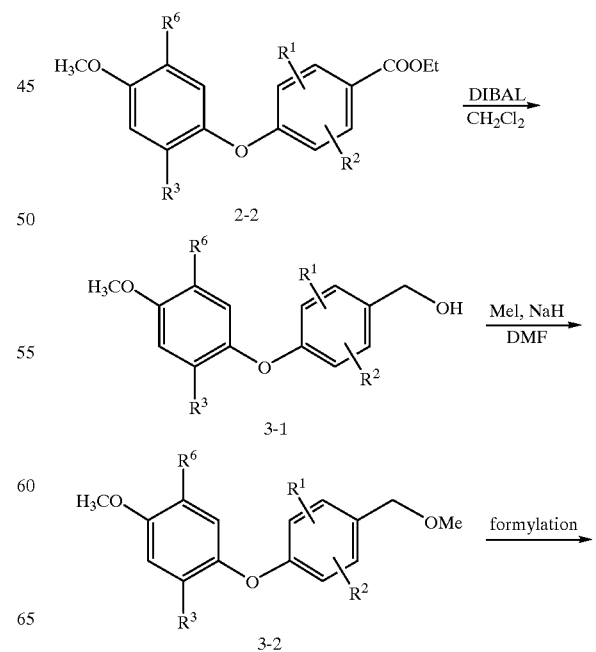

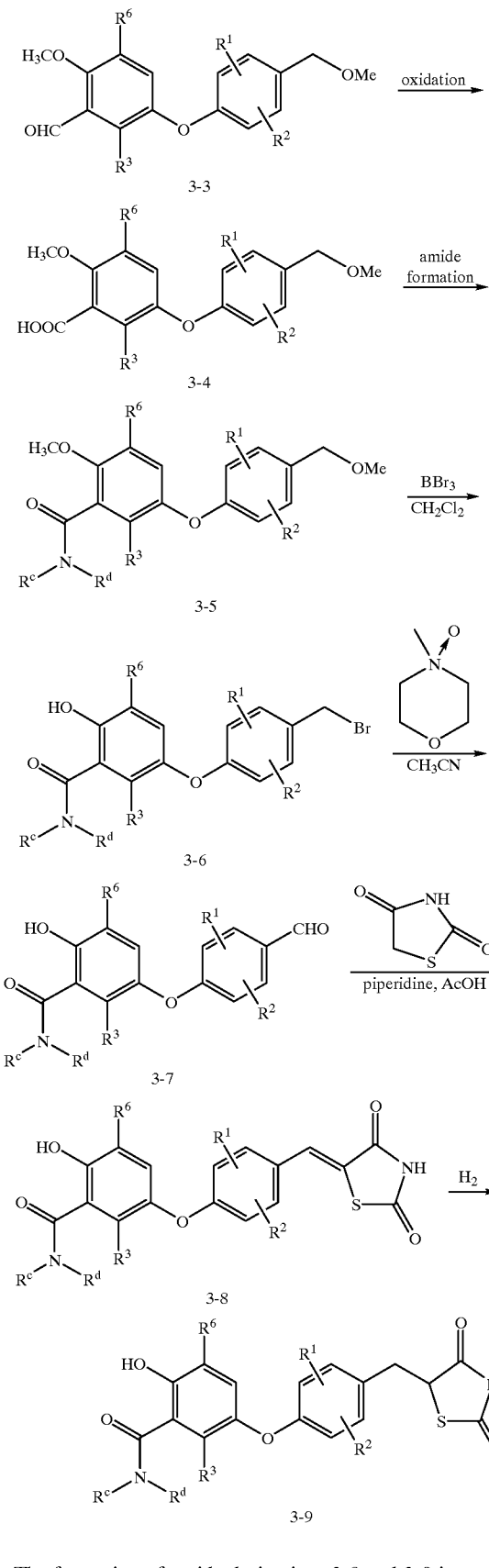

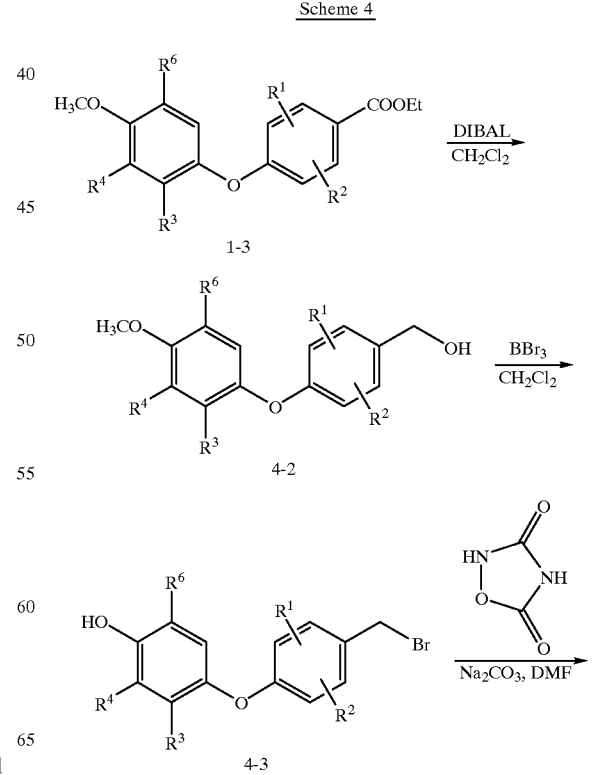

the corresponding alcohol 3-1 according to methods that will be well known to one of ordinary skill in the art, for example DIBAL reduction. Protection of benzyl alcohol 3-1 by reaction with methyl iodide in the presence of sodium hydride in dimethylformamide (DMF) gives methyl benzyl ether 3-2. Formylation of ether 3-2 to furnish aldehyde 3-3 can be accomplished according to known methods, for example, by treatment of ether 3-2 with hexamethylenetetramine at 65° C. in trifluoroacetic acid. Oxidation of 3-3 to the corresponding carboxylic acid 3-4 can also be performed according to conventional methods. Generally preferred oxidation methods include the use of Jones' reagent, i.e. chromic acid/aqueous sulfuric acid, or, alternatively, those methods employing sodium hypochlorite, for example, buffered aqueous NaClO and 2-methyl-2-butene in tert-butanol/tetrahydrofuran. The carboxylic acid 3-4 can be converted into carboxamide 3-5 according to known methods, for example, by reaction of the acid chloride or the mixed anhydride of carboxylic acid 3-4 with a primary or secondary amine in a dry, aprotic solvent such as dichloromethane, tetrahydrofuran (THF), dimethoxyethane (DME), or diethoxyethane (DEE) in the presence of a base such as TEA, dimethylaminopyridine (DMAP), or pyridine. Alternatively, carboxylic acid 3-4 can be reacted with N-hydroxysuccinimide, dicyclohexylcarbodiimide, and an amine in the presence of a base such as TEA in 1,2-dimethoxyethane. Demethylation of 3-5 with boron tribromide provides benzyl bromide 3-6. Oxidation of benzyl bromide 3-6 with N-methylmorpholine N-oxide in acetonitrile yields benzaldehyde 3-7 which is converted into benzyl thiazolidinedione 3-9 by Knoevenagel condensation followed by hydrogenation.

The formation of amide derivatives 3-8 and 3-9 is carried out as shown in Scheme 3. The ester 2-2 can be reduced to

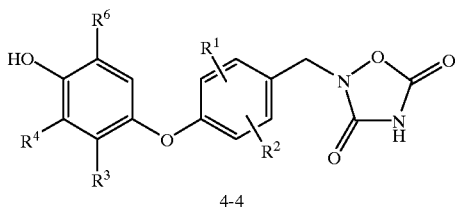

The preparation of oxadiazolidinedione derivatives 4-4 can be effected as outlined in Scheme 4. Reduction of compound 1-3 with DIBAL affords benzyl alcohol 4-2. Treatment of 4-2 with boron tribromide in dichloromethane furnishes benzyl bromide 4-3. Reaction of benzyl bromide 4-3 with oxadiazolidinedione in the presence of sodium carbonate in DMF yields benzyl oxazolidinedione 4-4.

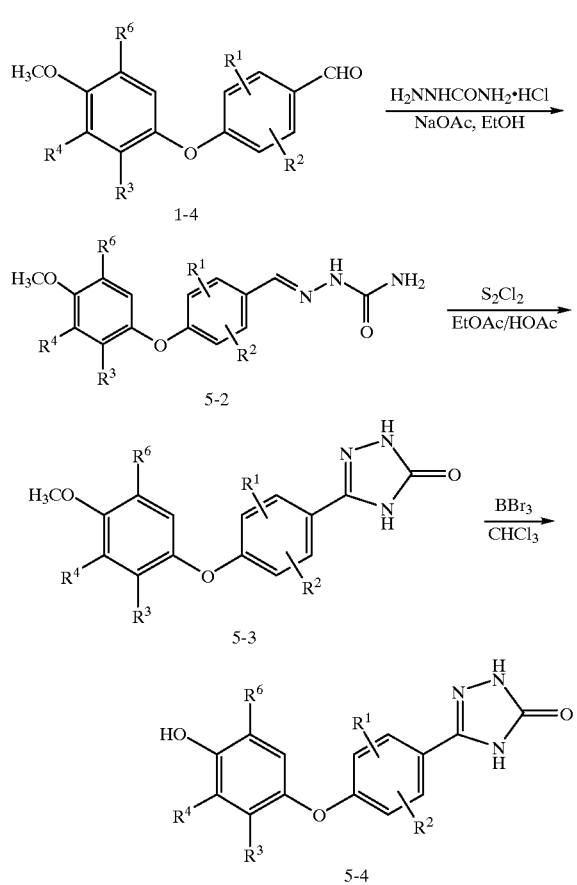

The formation of triazolone derivatives 5-4 is illustrated in Scheme 5. Treatment of benzaldehyde 1-4 with semicarbazide in the presence of sodium acetate affords the corresponding semicarbazone 5-2. Cyclization of semicarbazone 5-2 with sulfur monochloride in a mixture of ethyl acetate and acetic acid gives triazolone 5-3 which is subsequently demethylated with boron tribromide to furnish hydroxy compound 5-4.

The present invention is illustrated by the following Examples. It is to be understood, however, that the instant Examples are offered by way of illustrations of the invention and are not to be construed in any manner as limitations thereof.

EXPERIMENTAL

Chemical Syntheses

Throughout the present description, the following abbreviations or acronyms are used with the indicated meanings:

| | |
|---|---|
| AcOH | acetic acid |
| APCl+ | atmospheric pressure chemical ionization, positive ion mode |
| APCl− | atmospheric pressure chemical ionization, negative ion mode |
| Calc | Calculated |
| DEE | diethoxyethane |
| DME | dimethoxyethane |
| DMF | N,N-dimethylformamide |
| DMSO | dimethyl sulfoxide |
| ES+ | electrospray ionization, positive ion mode |
| Et | ethyl |
| EtOAc | ethyl acetate |
| EtOH | ethanol |
| Equiv | equivalent(s) |
| Hex | hexanes |
| KHMDS | potassium bis(trimethylsilyl)amide |
| Me | methyl |
| MeOH | methanol |
| MS | mass spectrometry |
| MSA | methanesulfonic acid |
| NMP | 1-methylpyrrolidone |
| NMR | nuclear magnetic resonance |
| RT | room temperature |
| TEA | triethylamine |
| TES | triethylsilane |
| TFA | trifluoroacetic acid |
| THF | tetrahydrofuran |
| TLC | thin layer chromatography |

The following synthetic Examples are illustrative of those procedures shown and described hereinabove for the sequential preparation of compounds 1-3 through 1-7 depicted generically in Scheme 1.

EXAMPLE 1

5-[3,5-Dichloro-4-(4-hydroxy-3-isopropyl-phenoxy)-benzyl]-thiazolidine-2,4-dione Step A 3,5-Dichloro-4-(3-isopropyl-4-methoxy-phenoxy)-benzoic acid ethyl ester The title compound was prepared from bis-(3-isopropyl-4-methoxy-phenyl)-iodonium tetrafluoroborate and 3,5-dichloro-4-hydroxy-benzoic acid ethyl ester in the presence of copper bronze and triethylamine by the methodologies described in Med. Chem., 38, 695–707 (1995). MS (APCl+) Calc.: 382.1, Found: 383.0 (M+1).

Step B 3,5-Dichloro-4-(3-isopropyl-4-methoxy-phenoxy)-benzaldehyde

To a solution of the product of Step A (100 mg, 0.26 mmol) in dichloromethane (3 ml) at 0° C. under dry nitrogen was added diisobutylaluminum hydride (1M in hexanes, 0.6 ml, 0.6 mmol) slowly over a period of about one minute with stirring. The reaction mixture was allowed to warm to room temperature and stirred for one hour. The reaction was quenched with methanol, followed by the addition of potassium tartrate (5 ml, 0.5 N) and the mixture was extracted with methylene chloride (3×10 ml). The combined extracts were dried, filtered, and concentrated to furnish the crude intermediate alcohol as an oil. To a solution of the crude alcohol in methylene chloride (5 ml) was added manganese dioxide (450 mg). After stirring at room temperature for about 2.5 hours, the reaction mixture was filtered through diatomaceous earth, and the filter cake was washed with hot methylene chloride (3×10 ml). The filtrates were combined and concentrated to furnish the title product as a solid that was used in the next step without purification. MS (APCl⁻) Calc.: 338.0, Found: 336.9 (M−1).

Step C
5-[3,5-Dichloro-4-(3-isopropyl-4-methoxy-phenoxy)-benzylidene]-thiazolidine-2,4-dione To a suspension of the title compound from Step B (60 mg, 0.18 mmol) and thiazolidinedione (21 mg, 0.18 mmol) in dry toluene (2 ml) was added a catalytic amount of piperidinium acetate which was generated by the addition of piperidine (1.5 mg, 0.018 mmol) and acetic acid (1.1 mg, 0.018 mmol). The mixture was heated to reflux under nitrogen for two hours. The solution was cooled, diluted with ethyl acetate (15 ml), washed with 1 N HCl (3×10 ml) and brine (10 ml), dried, filtered, and concentrated. The residue was purified by preparative TLC (5% methanol in dichloromethane) to give the title compound (26.1 mg) as a yellow solid. MS (APCl⁻) Calc.: 437.0, Found: 436.1 (M−1).

Step D
5-[3,5-Dichloro-4-(4-hydroxy-3-isopropyl-phenoxy)-benzylidene]-thiazolidine-2,4-dione To a solution of the title compound from Step C (26 mg, 0.060 mmol) in dichloromethane (1 ml) at room temperature was added boron tribromide (1M in dichloromethane, 0.12 ml, 0.12 mmol). After the addition, a brown solution was obtained which was stirred at room temperature for about three hours. An additional 4 equivalents of boron tribromide was added and the mixture was stirred for 15 minutes at room temperature. A brown precipitation formed. The reaction was quenched with water (5 ml) and extracted with dichloromethane (3×10ml). The combined extracts were dried, filtered, and concentrated, and the residue was purified by preparative TLC (7% methanol in dichloromethane) to give the title compound (13 mg) as an off-white solid. MS (APCl⁻) Calc: 423.0, Found: 422.0 (M−1).

Step E
5-[3,5-Dichloro-4-(3-isopropyl-4-methoxy-phenoxy)-benzyl]-thiazolidine-2,4-dione To a solution of the title compound from Step D (31 mg, 0.072 mmol) was dissolved in ethyl acetate/methanol (1 ml/1 ml) and placed in a hydrogenation bottle with 10% palladium on carbon (90 mg). The mixture was placed on Parr shaker for two hours under 50 p.s.i. of hydrogen, then filtered through diatomaceous earth, and the filter cake was washed with ethyl acetate/methanol. The combined filtrate was concentrated to give the title compound (26 mg) as a clear, viscous oil that was used in the next step without purification. MS (APCl⁻) Calc: 439.0, Found: 438.1 (M−1).

Step F
5-[3,5-Dichloro-4-(4-hydroxy-3-isopropyl-phenoxy)-benzyl]-thiazolidine-2,4-dione To a solution of the title compound from Step E (26 mg, 0.058 mmol) in dichloromethane (1 ml) at room temperature was added boron tribromide (1M in dichloromethane, 0.12 ml, 0.12 mmol). A tan precipitation was immediately formed. After stirring at room temperature for about 30 minutes, the mixture was quenched with water (5 ml), and extracted with dichloromethane (3×10 ml). The combined extracts were dried, filtered, and concentrated. The residue was purified by preparative TLC (7% methanol in dichloromethane) to afford the title compound (19 mg) as a solid. MS (APCl⁻) Calc: 425.0, Found: 424.0 (M−1).

Using appropriate starting materials, Examples 2 and 3 were prepared in an analogous manner to the sequence of reactions described for Example 1 as appropriate.

EXAMPLE 2

5-[4-(4-Hydroxy-3-isopropyl-phenoxy)-3,5-dimethyl-benzylidene]-thiazolidene-2,4-dione; MS (APCl⁻) Calc: 383.1, Found: 382.3 (M−1)

EXAMPLE 3

5-[4-(4-Hydroxy-3-isopropyl-phenoxy)-3,5-dimethyl-benzyl]-thiazolidine-2,4-dione; MS (APCl⁻) Calc: 385.1, Found: 384.2 (M−1)

The following synthetic Examples are illustrative of those procedures shown and described hereinabove for the sequential preparation of compounds 2-3 through 2-6 depicted generically in Scheme 2.

EXAMPLE 4

N-Cyclopropyl-5-[2,6-dichloro-4-(2,4-dioxo-thiazolidin-5-ylmethyl)-phenoxy]-2-hydroxy-benzenesulfonamide Step A
3,5-Dichloro-4-(4-methoxy-phenoxy)-benzoic acid ethyl ester To a solution of bis-(4-methoxyphenyl)iodonium tetrafluoroborate (15 g, 35 mmol) and copper bronze (3.0 g, 46.7 mmol) in methylene chloride (30 ml) at 0° C. was added dropwise a solution of 3,5-dichloro-4-hydroxy-benzoic acid ethyl ester (5.50 g, 23 mmol) and triethylamine (3.6 ml, 26 mmol) in dichloromethane (30 ml). The resulting mixture was stirred in the dark at room temperature for about five days and then filtered through a short pad of silica gel eluting with 3% ethyl acetate to remove baseline material. The filtrate was concentrated and the residue was dissolved in ether (30 ml). The product was crystallized to furnish the title compound as a solid (4.8 g). The filtrate was concentrated and purified by chromatography to furnish an additional 1.57 g of product. The total yield for the reaction was 81%. MS (APCl⁺) Calc: 340.0, Found: 314.8 (M+1, -Et).

Step B
3,5-Dichloro-4-(4-methoxy-phenoxy)-benzaldehyde

The title compound was prepared from 3,5-dichloro-4-(4-methoxy-phenoxy)-benzoic acid ethyl ester according to the procedure described in Example 1, Step B. MS (APCl⁻) Calc: 297.1, Found: 296.0 (M−1).

Step C
5-[3,5-Dichloro-4-(4-methoxy-phenoxy)-benzylidene]-thiazolidine-2,4-dione)

To a solution of the title compound of Step B (284 mg, 0.96 mmol) in toluene (16 ml) was added 2,4-thiazolidinedione (140 mg, 1.2 mmol), a catalytic amount of piperidinium acetate which was generated from piperidine (five drops) and acetic acid (five drops) and 4 Å molecular sieves. The mixture was stirred under reflux for about four hours, cooled to room temperature, filtered and concentrated. The product was purified by preparative TLC (4% methanol in dichloromethane) to afford the title compound (153 mg). MS (APCl⁻) Calc: 395.0, Found: 394.0 (M−1).

Step D
5-[3,5-Dichloro-4-(4-methoxy-phenoxy)-benzyl]-thiazolidine-2,4-dione

The title compound of Step C (93 mg) was dissolved in ethyl acetate/methanol (4 ml/2 ml) and then 10% palladium on carbon (70 mg) was added. The reaction mixture was placed on Parr shaker for four hours under 50 psi hydrogen at room temperature. The solution was filtered through diatomaceous earth, and concentrated. The residue was purified by preparative TLC (3% methanol in dichloromethane) to afford the title compound (52 mg) as a solid. MS (APCl⁻) Calc: 397.0, Found: 396.0 (M−1).

Step E
5-[2,6-Dichloro-4-(2,4-dioxo-thiazolidin-5-ylmethyl)-phenoxy]-2-methoxy-benzenesulfonyl chloride The title compound of Step D (52 mg, 0.13 mmol) was cooled to 0° C. and chlorosulfonic acid (0.5 mL) was added. The mixture was warmed to room temperature and stirred for about 1.5 hours. The solution was poured into ice (75 g), stirred until the ice had melted, and then extracted with ethyl acetate (3×25 ml). The combined extracts were washed with brine, dried over sodium sulfate, filtered and concentrated to afford the title compound (38.0 mg) as a brownish solid which was used in the next step without purification.

Step F
N-Cyclopropyl-5-[2,6-dichloro-4-(2,4-dioxo-thiazolidin-5-ylmethyl)-phenoxy]-2-methoxy-benzenesulfonamide To the title compound of Step E (38 mg, 0.08 mmol) in dry tetrahydrofuran (1 ml) at room temperature was added cyclopropylamine (8.0 mL, 0.12 mmol) and N-methylmorpholine (17 ml, 0.15 mmol). The reaction mixture was stirred at room temperature for two hours, quenched with 1N HCl (15 ml), and extracted with ethyl acetate (3×15 ml). The combined extracts were washed with 1N HCl (2×15 ml), brine (15 ml), dried over sodium sulfate, filtered, and concentrated. The residue was purified by preparative TLC (8% methanol in dichloromethane) to afford the title compound (16 mg, 41% yield). MS (APCl⁺) Calc: 516.0, Found: 516.9 (M+1).

Step G
N-Cyclopropyl-5-[2,6-dichloro-4-(2,4-dioxo-thiazolidin-5-ylmethyl)-phenoxy]-2-hydroxy-benzenesulfonamide To a solution of the title compound of Step F (16 mg, 0.032 mmol) in dichloromethane (0.5 ml) at 0° C. was added boron tribromide (1M in dichloromethane, 0.06 ml, 0.06 mmol). The reaction mixture was stirred at room temperature for one hour, then quenched by addition of 1N HCl (5 ml). The resulting solution was extracted with dichloromethane (3×5 ml). The combined extracts were dried over sodium sulfate, filtered, and concentrated. The residue was purified by preparative TLC (7% methanol in dichloromethane) to afford the title compound (11 mg, 68% yield) as a white solid. MS (APCl⁻) Calc: 502.0, Found: 501.2 (M−1).

The following synthetic Examples are illustrative of those procedures shown and described hereinabove for the sequential preparation of compounds 3-1 through 3-9 depicted generically in Scheme 3.

EXAMPLE 5

N-Cyclobutyl-5-[2,6-dichloro-4-(2,4-dioxo-thiazolidin-5ylmethyl)-phenoxy]-2-hydroxy-N-methyl-benzamide Step A
[3,5-Dichloro-4-(4-methoxy-phenoxy)-phenyl]-methanol To a solution of 3,5-dichloro-4-(4-methoxy-phenoxy)-benzoic acid ethyl ester (1.36 g, 4.01 mmol) in dichloromethane (35 ml) at 0° C. was added diisobutylaluminun hydride (1M in toluene, 12 ml, 12 mmol) and the mixture was stirred for 2.5 hours at 0° C. The reaction mixture was quenched with potassium sodium tartrate tetrahydrate (0.5 M aqueous solution, 50 ml), stirred for 20 minutes at room temperature and then was filtered through diatomaceous earth. The filtrate was concentrated and then taken up in water (60 ml). The aqueous solution was extracted with ethyl acetate (4×60 ml). The combined extracts were dried, filtered, and concentrated. The residue was purified by flash column chromatography (2% ethyl acetate in dichloromethane) to afford the title compound (871 mg). NMR (400 MHz, CDCl₃) δ7.39 (s, 2H), 6.74–6.82 (m, 4H), 4.69 (d, 2H), 3.76 (s, 3H), 1.83 (t, 1 H).

Step B
4-(2,6-dichloro-4-methoxymethyl-phenoxy)-anisole

To a solution of the title compound of Step A (400 mg, 1.34 mmol) in dry dimethylformamide (13 mL) at 0° C. under nitrogen was added NaH (60% dispersion in mineral oil, 134 mg, 3.3 mmol). After stirring for 30 minutes at 0° C. until hydrogen evolution ceased, methyl iodide (949 mg, 6.61 mmol) was added. The reaction mixture was warmed to room temperature and stirred for about 19 hours. The solution was poured into water (100 ml) and extracted with ethyl acetate (3×100 ml). The combined extracts were washed with 1M HCl (3×100 ml), brine (100 ml), dried, filtered, and concentrated. The crude product was purified by preparative TLC (30% hexane in dichloromethane) to afford the title compound (410 mg). NMR (400 MHz, CDCl₃) δ7.36 (s, 2H), 6.75–6.83 (m, 4H), 4.40 (s, 2H), 3.75 (s, 3H), 3.43 (s, 3H).

Step C
5-(2,6-Dichloro-4-methoxymethyl-phenoxy)-2-methoxy-benzaldehyde

A mixture of the title compound of Step B (410 mg, 1.31 mmol), hexamethylenetetramine (256 mg, 2.0 mmol) and trifluoroacetic acid (2.5 ml) under nitrogen was heated to 75° C. and stirred for about three hours. The solution was concentrated in vacuo to give a yellow viscous oil. Water (20 ml) was added to the yellow oil and the mixture was stirred for about 30 minutes at room temperature. The aqueous solution was neutralized with saturated sodium bicarbonate and extracted with ethyl acetate (3×30 ml). The combined organic extracts were washed with saturated sodium bicarbonate (2×50 ml), brine (50 ml), dried, filtered and concentrated to give the title compound (440 mg ) as a crude product which was used in the next step without further purification. NMR (400 MHz, CDCl₃) δ10.36 (s, 1H), 7.33 (s, 2H), 7.11–7.16 (m, 2H), 6.93 (d, 1H), 4.39 (s, 2H), 3.86 (s, 3H), 3.40 (s, 3H).

Step D
5-(2,6-Dichloro-4-methoxymethyl-phenoxy)-2-methoxy-benzoic acid

To a solution of the title compound of Step C (228 mg, 0.67 mmol) and 2-methyl-2-butene (2M in tetrahydrofuran, 5 ml, 10.0 mmol) in tert-butanol/tetrahydrofuran (1 ml/3 ml) was added slowly a solution of sodium hypochlorite (543 mg, 6.0 mmol) in potassium dihydrogen phosphate aqueous solution (0.6 M, 8 ml). The reaction mixture was stirred for one hour at room temperature. The mixture was acidified with 1N HCl and extracted with ethyl acetate (3×20 ml). The combined organic extracts were washed with 1N HCl (2×40 ml), brine (40 mL), dried, filtered, and concentrated to afford the title compound (241 mg) as a viscous oil which was used in the next step without further purification. MS (APCl⁻) Calc: 356.0, found: 355.0 (M−1).

Step E
N-Cyclobutyl-5-(2,6-dichloro-4-methoxymethyl-phenoxy)-2-methoxy-benzamide To a solution of the title compound of Step D (238 mg, 0.67 mmol) in tetrahydrofuran (7 ml) at 0° C. under nitrogen was added isobutylchloroformate (0.13 mL, 1 mmol) and N-methylmorpholine (0.15 ml, 1.3 mmol). After stirring for about 30 minutes at 0° C., cyclobutylamine (0.11 ml, 1.3 mmol) was added. The reaction mixture was warmed to room temperature and stirred for about 19 hours. The reaction solution was diluted with 1N HCl (30 ml) and extracted with ethyl acetate (3×15 ml). The combined organic extracts were washed with 1N HCl (2×50 ml), brine (50 ml), dried, filtered, and concentrated. The crude product was purified by preparative TLC (50% ethyl acetate in hexanes) to afford the title compound (170 mg) as a viscous oil. MS (APCl$^+$) Calc: 409.1, found: 409.7 (M+1)

Step F
N-Cyclobutyl-5-(2,6-dichloro-4-methoxymethyl-phenoxy)-2-methoxy-N-methyl-benzamide To a solution of the title compound of Step E (170 mg, 0.41 mmol) in dimethylformamide (4 ml) at 0° C. under nitrogen was added sodium hydride (60% dispersion in mineral oil, 41 mg, 1 mmol). The resulting slurry mixture was stirred at 0° C. for about 30 minutes and gradually became a brownish-yellow solution. To this solution at 0° C. was added methyl iodide (0.13 ml, 2 mmol). The resulting solution was warmed to room temperature and stirred for about 19 hours. The solution was diluted with 1N HCl (30 ml) and extracted with ethyl acetate (3×15 ml). The combined organic extracts were washed with 1N HCl (3×50 ml), brine, dried, filtered, and concentrated. The residue was purified by preparative TLC (50% ethyl acetate in hexanes) to afford the title compound (155 mg). MS (APCl$^+$) Calc: 423.1, found: 424.0 (M+1).

Step G
5-(4-Bromomethyl-2,6-dichloro-phenoxy)-N-cyclobutyl-2-hydroxy-N-methyl-benzamide To a solution of the title compound of Step F in dichloromethane (2.2 ml) at room temperature was added boron tribromide (1M in dichloromethane, 1.5 ml, 1.5 mmol). The reaction mixture was stirred at room temperature for about two hours, and quenched with water (20 ml). After stirring for about 15 minutes, the solution was extracted with dichloromethane (3×15 ml). The combined organic extracts were washed with brine (50 ml), treated with activated carbon, filtered through diatomaceous earth, dried and concentrated to give the title compound (163 mg) as an off-white solid which was used in the next step without further purification. MS (APCl$^-$) Calc: 457.0, found: 456.0 (M−1).

Step H
N-Cyclobutyl-5-(2,6-dichloro-4-formyl-phenoxy)-2-hydroxy-N-methyl-benzamide To a solution of the title compound of Step G (130 mg, 0.28 mmol) in dry acetonitrile (6 ml) at room temperature under nitrogen was added molecular seives (4 A°, 50 mg). After stirring for about 15 minutes at room temperature, N-methylmorpholine N-oxide (66 mg, 0.57 mmol) was added. The resulting mixture was stirred at room temperature for about 18 hours, then filtered through a short pad of silica gel with an acetonitrile wash. The filtrate was concentrated to afford the title compound (88 mg) as an off-white foam which was used in the next step without further purification. MS (APCl$^-$) Calc: 393.1, found: 392.1 (M−1).

Step I
N-Cyclobutyl-5-[2,6-dichloro-4-(2,4-dioxo-thiazolidin-5-ylidenemethyl)-phenoxy]-2-hydroxy-N-methyl-benzamide To a solution of the title compound of Step H (40 mg, 0.10 mmol) and thiazolidinedione (13 mg, 0.11 mmol) in toluene (2 ml) was added acetic acid (1.5 µl, 0.025 mmol), piperidine (2.5 µl, 0.025 mmol) and powdered 3 A° molecular sieves. The reaction mixture was heated to reflux and stirred at reflux for about 18 hours. The solvent was removed under reduced pressure and the residue was partitioned between ethyl acetate (10 ml) and water (10 ml). The organic layer was washed with 1N HCl (2×10 ml), brine (10 ml), dried, filtered, and concentrated. The crude product was purified by preparative TLC (7% MeOH in dichloromethane) to afford the title compound (37 mg). MS (APCl$^-$) Calc: 492.0, found: 491.0 (M−1).

Step J
N-Cyclobutyl-5-[2,6-dichloro-4-(2,4-dioxo4hiazolidin-5-ylmethyl)-phenoxy]-2-hydroxy-N-methyl-benzamide To a solution of the title compound of Step I (35 mg, 0.073 mmol) in ethyl acetate/methanol (4 ml/1 ml) in a hydrogenation bottle was added 10% palladium on carbon (70 mg). The solution was placed on Parr shaker for one hour under 55 psi of hydrogen at room temperature, then filtered through diatomaceous earth. The filtrate was concentrated to afford the title compound (13 mg) as a yellow solid. MS (APCl$^-$) Calc: 494.0, found: 493 (M−1).

The following synthetic Examples are illustrative of those procedures shown and described hereinabove for the sequential preparation of compounds 4-2 through 4-4 depicted generically in Scheme 4.

EXAMPLE 6

2-[3,5-Dichloro-4-(4-hydroxy-3-isopropyl-phenoxy)-benzyl]-[1,2,4]oxadiazolidine-3,5-dione Step A
[3,5-Dichloro-4-(3-isopropyl-4-methoxy-phenoxy)-phenyl]-methanol To a solution of 3,5-dichloro-4-(3-isopropyl-4-methoxy-phenoxy)-benzoic acid ethyl ester (prepared as described in Example 1, Step A) (100 mg, 0.26 mmol) in methylene chloride (3 mL) at −78° C. under nitrogen was added diisobutylaluminum hydride (1M in hexane, 0.6 ml, 0.6 mmol). The reaction mixture was warmed to room temperature and stirred for about 19 hours. The reaction was quenched with methanol (1 ml) and sodium potassium tartrate (0.5M aqueous solution, 2 ml). After stirring for about 15 minutes, the solution was extracted with methylene chloride (3×10 mL). The combined organic extracts were washed with saturated sodium bicarbonate and brine, dried, filtered, and concentrated. The crude product was purified by preparative TLC (methylene chloride) to afford the title compound (75 mg) as a solid. NMR (400 MHz, CDCl$_3$) δ7.39 (s, 2H), 6.85 (d, 1H), 6.69 (d, 1H), 6.43–6.46 (dd, 1H), 4.68 (s, 2H), 3.77 (s, 3H), 3.26–3.30 (sept, 1H), 2.03 (bs, 1H), 1.18 (d, 6H).

Step B
4-(4-Bromomethyl-2,6-dichloro-phenoxy)-2-isopropyl-phenol

To a solution of the title compound of Step A (75 mg, 0.22 mmol) in dry methylene chloride (2 ml) at room temperature under nitrogen was added boron tribromide (1M in methylene chloride, 0.44 ml, 0.44 mmol). The reaction mixture was stirred at room temperature for about one hour, quenched with water (5 ml) and extracted with methylene chloride (3×5 ml). The combined organic exrtracts were dried, filtered, and concentrated. The crude product was purified by preparative TLC (methylene chloride) to afford the title compound (59 mg) as an oil. MS (APCl$^-$) Calc: 388.0, found: 386.9 (M−1).

Step C
2-[3,5-Dichloro-4-(4-hydroxy-3-isopropyl-phenoxy)-benzyl]-[1,2,4]oxadiazolidine-3,5-dione The title compound was prepared according to the methodology described in *Synthesis*, 265–266 (1991).

To a solution of the title compound of Step B (59 mg, 0.15 mmol) and [1,2,4]oxadiazolidine-3,5-dione (16 mg, 0.15 mmol) in DMF (1.5 ml) at room temperature was added sodium carbonate (32 mg, 0.30 mmol). After stirring at room temperature for about two hours, the solution was diluted with 0.5N HCl (10 ml) and extracted with ethyl acetate (3×10 ml). The combined organic extracts were washed with water (3×15 ml), brine (15 ml), dried, filtered, and concentrated. The crude product was purified by preparative TLC (22% methanol/3.5% water/74.5% chloroform) to afford the title compound (61 mg). MS (APCl$^-$) Calc: 410.0, found: 409.1 (M−1).

Using appropriate starting materials, Examples 7 and 8 were prepared in an analogous manner to the sequence of reactions described for Example 6 as appropriate.

EXAMPLE 7

2-[4-(3-isopropyl-4-methoxy-phenoxy)-3,5-dimethyl-benzyl]-[1,2,4]oxadiazolidine-3,5-dione, MS (APCl$^-$) Calc: 384.2, found: 383.2 (M−1).

EXAMPLE 8

2-[4-(4-Hydroxy-3-isopropyl-phenoxy)-3,5-dimethyl-benzyl]-[1,2,4]oxadiazolidine-3,5-dione, MS (APCl$^-$) Calc: 370.2, found: 369.2 (M−1).

The following synthetic Examples are illustrative of those procedures shown and described hereinabove for the sequential preparation of compounds 5-2 through 5-4 depicted generically in Scheme 5.

EXAMPLE 9

5-[4-(4-Hydroxy-3-isopropyl-phenoxy)-3,5-dimethyl-phenyl]-2,4-dihydro-[1,2,4]triazol-3-one Step A
3,5-dimethyl-4-(3-isopropyl-4-methoxy-phenoxy)-benzaldehyde-semicarbazone To a solution of 4-(3-isopropyl-4-methoxy-phenoxy)-3,5-dimethyl-benzaldehyde (19 mg, 0.063 mmol) in ethanol (1 ml) at room temperature was added semicarbazide (7.7 mg, 0.69 mmol) and sodium acetate (5.1 mg, 0.063 mmol). After stirring at room temperature for about one hour, the solvent was removed under vacuum, and the residue was dissolved in ethyl acetate (5 ml). The ethyl acetate solution was washed with water (3×5 ml), brine (5 ml), dried, filtered, and concentrated to afford the title compound (20 mg) as a yellow solid which was used directly in the next step without further purification. MS (APCl$^-$) Calc: 355.2, found: 354.3 (M−1).

Step B
5-[4-(3-isopropyl-4-methoxy-phenoxy)-3,5-dimethyl-phenyl]-2,4-dihydro-[1,2,4]triazol-3-one A solution of the title compound of Step A (20 mg, 0.055 mmol) and sulfur monochloride (26.7 µl, 0.33 mmol) in ethyl acetate/acetic acid (2.4 ml/0.6 ml) was heated to reflux for about eight hours. The mixture was concentrated and the residue was purified by preparative TLC (5% methanol in dichloromethane) to afford the title compound (4.7 mg) as a white solid. MS (APCl$^+$) Calc: 353.2, found: 354.2 (M+1).

Step C
5-[4-(4-Hydroxy-3-isopropyl-phenoxy)-3,5-dimethyl-phenyl]-2,4-dihydro-[1,2,4]triazol-3-one To a solution of the title compound of Step B (4.7 mg, 0.013 mmol) in chloroform (0.5 ml) was added boron tribromide (1M in dichloromethane, 0.26 ml, 0.26 mmol) and the mixture was stirred at room temperature for about one hour. The reaction was quenched with water (5 ml), acidified with 1N HCl (1 ml), and extracted with ethyl acetate (3×10 ml). The combined organic extracts were dried, filtered, and concentrated to afford the title compound (4.2 mg). MS (APCl$^-$) Calc: 339.2, found: 338.3 (M−1).

Biological Assays

The utility of the compounds of Formula (I), the stereoisomers and prodrugs thereof, and the pharmaceutically acceptable salts of the compounds, stereoisomers, and prodrugs in the practice of the instant invention, can be evidenced by activity in at least one of the assays described hereinbelow.

ASSAY 1

Oxygen Consumption

As will be well known to one of ordinary skill in the art, during increased energy expenditure, animals generally consume increased amounts of oxygen. In addition, metabolic fuels such as, for example, glucose and fatty acids, are oxidized to $CO_2$ and $H_2O$ with the concomitant evolution of heat, an effect commonly referred to in the art as thermogenesis. Accordingly, the measurement of oxygen consumption in animals, including humans and companion animals, is an indirect measure of thermogenesis, and indirect calorimetry may be commonly used in animals, e.g., humans, by one of ordinary skill in the art, to measure such energy expenditures.

One of ordinary skill in the art will appreciate that increased energy expenditure and the concomitant burning of metabolic fuels resulting in the production of heat may be efficacious with respect to the treatment of, e.g., obesity. As will be well known to one of ordinary skill in the art, thyroid hormones affect cardiac functioning, for example, by causing an increase in the heart rate and, accordingly, an increase in oxygen consumption with concomitant heat production.

The ability of the compounds of Formula (I), the stereoisomers and prodrugs thereof, and the pharmaceutically acceptable salts of the compounds, stereoisomers, and prodrugs, to generate a thermogenic response may be demonstrated according to the following protocol.

A. Experimental

This in vivo protocol is designed to evaluate the efficacy and cardiac effects of compounds that are tissue-selective thyroid hormone agonists. The efficacy endpoints measured are whole body oxygen consumption and the activity of liver mitochondrial alpha-glycerophosphate dehydrogenase ("mGPDH"). The cardiac endpoints that are measured are heart weight and heart mGPDH activity. The protocol involves: (a) dosing fatty Zucker rats for about 6 days, (b) measuring oxygen consumption and (c) harvesting tissue for preparation of mitochondria and subsequent assaying of enzyme activity thereby.

B. Preparation of Rats

Male fatty Zucker rats having a body weight range of from about 400 g to about 500 g are housed for from about 3 to about 7 days in individual cages under standard laboratory conditions prior to the initiation of the study.

A compound of Formula (I), or a stereoisomer or prodrug thereof, or a pharmaceutically acceptable salt of the stereoisomer or prodrug; vehicle; or $T_3$ sodium salt, is administered by oral gavage as a single daily dose given between about 3 p.m. to about 6 p.m. for about 6 days. A compound of Formula (I), or a stereoisomer or prodrug thereof, or a pharmaceutically acceptable salt of the stereoisomer or prodrug; vehicle; or $T_3$ sodium salt, is dissolved in a suitably small volume of about 1N NaOH and then brought up to a suitable volume with about 0.01N NaOH containing about 0.25% of methyl cellulose (10:1, 0.01N NaOH/MC:1N NaOH). The dosing volume is approximately 1 ml.

C. Oxygen Consumption

About 1 day after the last dose of the compound is administered, oxygen consumption is measured using an open circuit, indirect calorimeter (Oxymax, Columbus Instruments, Columbus, Ohio 43204). The Oxymax gas sensors are calibrated with $N_2$ gas and a gas mixture (about 0.5% of $CO_2$, about 20.5% of $O_2$, about 79% of $N_2$) before each experiment.

The subject rats are removed from their home cages and their body weights recorded. The rats are placed into the sealed chambers (43×43×10 cm) of the Oxymax calorimeter, the chambers are placed in the activity monitors, and the air flow rate through the chambers is then set at from about 1.61/min to about 1.71/min.

The Oxymax software then calculates the oxygen consumption (ml/kg/hour) of the rats based on the flow rate of air through the chambers and the difference in oxygen content at the inlet and output ports. The activity monitors have 15 infrared light beams spaced about one inch apart on each axis, and ambulatory activity is recorded when two consecutive beams are broken, and the results are recorded as counts.

Oxygen consumption and ambulatory activity are measured about every 10 minutes for from about 5 hours to about 6.5 hours. Resting oxygen consumption is calculated on individual rats by averaging the values excluding the first 5 values and the values obtained during time periods where ambulatory activity exceeds about 100 counts.

ASSAY 2

Binding to Thyroid Hormone Receptors

The ability of a compound of Formula (I), or a stereoisomer or prodrug thereof, or a pharmaceutically acceptable salt of the stereoisomer or prodrug, to bind to thyroid hormone receptors can be demonstrated in the following protocol.

A. Preparation of Insect Cell Nuclear Extracts

High Five cell pellets (BTI-TN-5B1-4, catalog number B855-02, Invitrogen®, Carlsbad, Calif.) obtained about 48 hours after infection with baculovirus (GibcoBRL®, Gaithersburg, Md.) expressing either human TRα or TRβ are suspended in ice cold Sample Buffer (10 mM Tris, pH 8.0; 1 mM $MgCl_2$; 1 mM DTT; 0.05% Tween 20; 1 mM 4-(2-aminoethyl)-benzenesulfonylfluoride; 25 µg/ml leupeptin). After about 10 minutes incubation on ice, the suspension is homogenized by 20 strokes with a Dounce homogenizer (VWR® Scientific Products, West Chester, Pa.) and centrifuged at 800×g for about 15 minutes at 4° C. The pellet (nuclei) is suspended in a hypertonic buffer (0.4 M KCl; 10 mM Tris, pH 8.0; 1 mM $MgCl_2$; 1 mM DTT; 0.05% Tween 20) and incubated for about 30 min on ice. The suspension is centrifuged at 100,000×g for about 30 minutes at 4° C. The supernatant (nuclear extract) is stored in 0.5 ml aliquots at −80° C.

B. Binding Assay

Competition binding assays to measure the interaction of the Formula (I) compounds with thyroid hormone receptor α1 and β1 (TRα and TRβ) are carried out according to the following protocol.

Solutions of the compounds of Formula (I), or the stereoisomers or prodrugs thereof, or the pharmaceutically acceptable salts of the stereoisomers or prodrugs (final compound concentration of 20 mM) are prepared using 100% DMSO as a solvent. The compound is serially diluted in an assay buffer (5 mM Tris-HCl, pH 8.0; 50 mM NaCl; 2 mM EDTA; 10% (v/v) glycerol; 1 mM DTT, "assay buffer") containing 0.4 nM $^{125}$I-$T_3$ (specific activity of about 2200 Ci/mmol) to yield solutions that vary in compound concentration from about 10 µM to about 0.1 nM.

High Five insect cell nuclear extract containing either TRα or TRβ is diluted to a total protein concentration of 0.0075 mg/ml using the assay buffer as diluent.

One volume (100 µl) of each Formula (I) compound dilution (containing 0.4 nM $^{125}$I-T3) is combined with an equal volume (100 µl) of diluted nuclear extract containing TRα1 or TRβ1, and incubated at RT for about 90 min. A one hundred and fifty µl sample of the binding reaction is removed and placed into a 96-well filter plate (Millipore®, Bedford, Mass.) that has been pre-washed with ice-cold assay buffer. The plate is subjected to vacuum filtration using a filtration manifold (Millipore®). Each well is washed five times by the addition of 200 µl of ice-cold assay buffer and subsequent vacuum filtration. The plate is removed from the vacuum filtration manifold, the bottom of the plate is briefly dried on paper towels, then 25 µl of Wallac® (EG&G Wallac®, Gaithersburg, Md.) Optiphase Supermix scintillation cocktail is added to each well and the top of the plate is covered with plastic sealing tape (Microplate Press-on Adhesive Sealing Film, Packard® Instrument Co., Inc., Downers Grove, Ill.) and the radioactivity is quantitated using a Wallac® Microbeta 96-Well plate scintillation counter.

What is claimed is:

1. A compound of Formula (I)

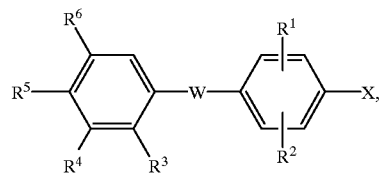

the stereoisomers and prodrugs thereof, and the pharmaceutically acceptable salts of said compounds, stereoisomers, and prodrugs, wherein:

W is oxygen, sulfur, —SO—, or —S(O)$_2$;

$R^1$ and $R^2$ are both methyl, bromo or chloro; and $R^1$ is located at the 3-position and $R^2$ is located at the 5-position;

$R^3$ is hydrogen;

$R^4$ is —(C$_1$–C$_{10}$)alkyl submitted with zero to two substituents independently selected from fluoro, hydroxy, oxo, aryl, heteroaryl, —(C$_3$–C$_8$)cycloalkyl, or heterocycloalkyl, —S(O)$_2$NR$^c$R$^d$, —C(O)NR$^c$R$^d$, —S(O)$_2$R$^c$, —(C$_3$–C$_8$)cycloalkyl, heterocycloalkyl, —C(O)R$^c$, —OR$^b$, —SR$^c$, —S(O)R$^c$, —NR$^a$C(O)R$^d$, —NR$^a$C(O)NR$^c$R$^d$, or —NR$^a$S(O)$_2$R$^d$;

$R^5$ is hydroxy;

$R^6$ is hydrogen;

$R^a$ for each occurence is independently hydrogen, or —(C$_1$–C$_6$)alkyl substituted with zero or one —(C$_3$–C$_6$) cycloalkyl or methoxy;

$R^b$ for each occurence is independently hydrogen, —(C$_1$–C$_{12}$)alkyl substituted with zero to three substituents independently selected from Group VI aryl, heteroalkyl, –(C$_3$–C$_{10}$)cycloalkyl, heterocycloalkyl, —C(O)NR$^c$R$^d$, or —C(O)R$^f$;

$R^c$ and $R^d$ for each occurrence are each independently hydrogen, ($C_1$–$C_{12}$)alkyl substituted with zero to three substituents independently selected from Group VI, —($C_2$–$C_{12}$)alkenyl, —($C_2$–$C_{12}$)alkynyl, aryl, heteroaryl, —($C_3$–$C_{10}$)cycloalkyl, or heterocycloalkyl; or $R^c$ and $R^d$ are taken together along with the atom(s) to which they are attached to form a 3–10 membered heterocylic ring which may optionally contain a second heterogroup selected from oxygen, —$NR^c$—, or sulfur, and wherein said heterocyclic ring is substituted with zero to four substituents independently selected from —($C_1$–$C_4$)alkyl, —$OR^b$, oxo, —CN, phenyl, or $R^e$ for each occurrence is hydrogen, —CN, —($C_1$–$C_{10}$) alkyl substituted with zero to three substituents independently selected from Group V, —($C_2$–$C_{10}$)alkenyl, —($C_2$–$C_{10}$)alkoxy, —($C_3$–$C_{10}$)cycloalkyl, aryl, heteroaryl, —C(O)$R^f$, —C(O)O$R^f$, —C(O)N$R^a R^f$, or —S(O)$_2 R^f$;

$R^f$ for each occurence is independently —($C_1$–$C_{10}$)alkyl substituted with zero to three substituents independently selected from Group VI, —($C_2$–$C_{12}$)alkenyl, —($C_2$–$C_{10}$)alkynyl, —($C_3$ $C_{10}$)cycloalkyl, aryl, heteroaryl, or heterocycloalkyl;

$R^g$ for each occurrence is independently hydrogen, —($C_1$–$C_6$)alkyl, —($C_1$–$C_6$)alkenyl, aryl, —C(O)$R^f$, —C(O)O$R^f$, —C(O)N$R^a R^f$, —S(O)$_2 R^f$, or —($C_3$–$C_8$) cycloalkyl;

Group V is halogen, —$CF_3$, —$OCF_3$, —OH, oxo, —($C_1$–$C_6$)alkoxy, —CN, aryl, heteroaryl, —($C_3$–$C_{10}$) cycloalkyl, heterocycloalkyl, —S$R^f$, —S(O)$R^f$, —S(O)$_2 R^f$, —S(O)$_2$N$R^a R^f$, —N$R^a R^g$, or —C(O) N$R^a R^f$;

Group VI is halogen, hydroxy, oxo, —($C_1$–$C_6$)alkoxy, aryl, heteroaryl, —($C_3$–$C_8$)cycloalkyl, heterocycloalkyl, —CN, or —$OCF_3$;

provided that when $R^4$ is —($C_1$–$C_{12}$)alkyl substituted with zero to two substituents independently selected from Group V, wherein said Group V substituent is oxo, said oxo group is substituted on a carbon atom other than the $C_1$ carbon atom in —($C_1$–$C_{12}$)alkyl;

aryl for each occurrence is independently phenyl or naphthyl substituted with zero to four substituents independently selected from halogen, —($C_1$–$C_6$)alkyl, —CN, —S$R^f$, —S(O)$R^f$, —S(O)$_2 R_f$, —($C_3$–$C_6$) cycloalkyl, —S(O)$_2$N$R^a R^f$, —N$R^a R^g$, —C(O)N$R^a R^f$, —O$R^b$, -perfluoro-($C_1$–$C_4$)alkyl, or —COO$R^f$;

provided that when said substituent(s) on aryl are —S$R^f$, —S(O)$R^f$, —S(O)$_2 R^f$, —S(O)$_2$N$R^a R^f$, —N$R^a R^f$, —C(O)N$R^a R^f$, —O$R^b$, or —COO$R^f$, said substituents $R^b$, $R^f$, and $R^g$, are other than aryl or heteroaryl;

heteroaryl for each occurence is independently a 5-, 6-, 7-, 8-, or 9-membered monocyclic or bicyclic ring having from one 10 three heteroatoms selected from O, N, or S;

wherein in said bicyclic ring, a monocyclic heteroaryl ring is fused to a benzene ring or to another heteroaryl ring, and having zero to three substituents independently selected from halogen, —($C_1$–$C_4$alkyl, —$CF_3$, —O$R^b$, —N$R^a R^g$, or —COO$R^f$;

provided that when said substituent(s) on heteroaryl are —N$R^a R^g$, —O$R^b$, or —COO$R^f$, said substituents $R^b$, $R^f$, and $R^g$, are other than aryl or heteroaryl;

heterocycloalkyl for each occurence is independently a 5-, 6-, 7-, 8-, or 9-membered monocycle or bicycle cycloalkyl ring having from one to three heteroatoms selected from oxygen, —$NR^e$, or sulfur, and having zero to Lour substituents independently selected from ($C_1$–$C_4$)alkyl, O$R^b$, oxo, —CN, phenyl, or —N$R^a R^g$; and X is

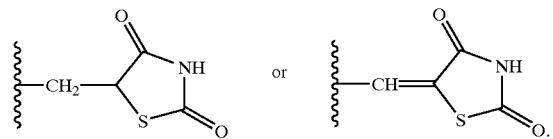

2. A compound of claim 1 selected from the group consisting of:

5-[3,5-dichloro-4-(4-hydroxy-3-isopropyl-phenoxy)-benzyl]-thiazolidine-2,4-dione;

5-[4-(4-hydroxy-3-isopropyl-phenoxy)-3,5-dimethyl-benzylidene]-thiazolidine-2,4-dione; and 5-[4-(4-hydroxy-3-isopropyl-phenoxy)-3,5-dimethyl-benzyl]thiazolidine-2,4-dione; the stereoisomers and prodrugs thereof, and the pharmaceutically acceptable salts of said compounds, stereoisomers, and prodrugs.

3. A method of treating a condition selected from the group consisting of obesity, overweight condition, hyperlipidemia, glaucoma, cardiac arrhythmias, skin disorders, thyroid disease, hypothyroidism, thyroid cancer, diabetes, atherosclerosis, hypertension, coronary heart disease, congestive heart failure, hypercholesteremia, depression and osteoporosis, in a mammal which method comprises administering to said mammal a therapeutically effective amount of a compound of Formula (I), a stereoisomer or prodrug thereof, or a pharmaceutically acceptable salt of said compound, stereoisomer or prodrug, as defined in claim 1.

4. A method according to claim 3 wherein said condition is obesity.

5. A method of treating a condition selected from the group consisting of obesity, overweight condition, hyperlipidemia, glaucoma, cardiac arrhythmias, skin disorders, thyroid disease, hypothyroidism, thyroid cancer, diabetes, atherosclerosis, hypertension, coronary heart disease, congestive heart failure, hypercholesteremia, depression and osteoporosis, which method comprises administering to a patient having, or at risk of having, a condition selected from the group consisting of obesity, overweight condition, hyperlipidemia, glaucoma, cardiac arrhythmias, skin disorders, thyroid disease, hypothyroidism, thyroid cancer, diabetes, atherosclerosis, hypertension, coronary heart disease, congestive heart failure, hypercholesteremia, depression and osteoporosis, a therapeutically effective amount of:

1) a compound of Formula (I), a stereoisomer or prodrug thereof, or a pharmaceutically acceptable salt of said compound, stereoisomer or prodrug, as defined in claim 1; and 2) an additional compound useful for treating a condition selected from the group consisting of obesity, overweight condition, hyperlipidemia, glaucoma, cardiac arrhythmias, skin disorders, thyroid disease, hypothyroidism, thyroid cancer, diabetes, atherosclerosis, hypertension, coronary heart disease, congestive heart failure, hypercholesteremia, depression and osteoporosis.

6. A method according to claim 1 wherein said condition is obesity.

7. A method according to claim 1 wherein said additional compound is a lipase inhibitor.

8. A method according to claim 7 wherein said lipase inhibitor is selected from the group consisting of lipstatin, tetrahydrolipstatin, FL-386, WAY-121898, Bay-N-3176, valilactone, esterastin, ebelactone A, ebelactone B and RHC 80267.

9. A method according to claim 5 wherein said additional compound is an anorectic agent.

10. A method according to claim 9 wherein said anorectic agent is selected from the group consisting of phentermine, sibutramine, fenfluramine, dexfenfluramine and bromocriptine.

11. A pharmaceutical composition comprising a compound of Formula (I), a stereoisomer or prodrug thereof, or a pharmaceutically acceptable salt of said compound, stereoisomer or prodrug, as defined in claim 1.

12. A kit for treating a condition selected from the group consisting of obesity, overweight condition, hyperlipidemia, glaucoma, cardiac arrhythmias, skin disorders, thyroid disease, hypothyroidism, thyroid cancer, diabetes, atherosclerosis, hypertension, coronary heart disease, congestive heart failure, hypercholesteremia, depression and osteoporosis, wherein said kit comprises:

a) a first pharmaceutical composition comprising a compound of Formula (I), a stereoisomer or prodrug thereof, or a pharmaceutically acceptable salt of said compound, stereoisomer or prodrug, as defined in claim 1;

b) a second pharmaceutical composition comprising an additional compound useful for treating a condition selected from the group consisting of obesity, overweight condition, hyperlipidemia, glaucoma, cardiac arrhythmias, skin disorders, thyroid disease, hypothyroidism, thyroid cancer, diabetes, atherosclerosis, hypertension, coronary heart disease, congestive heart failure, hypercholesteremia, depression and osteoporosis; and c) a container.

13. A pharmaceutical composition comprising a compound of Formula (I), a stereoisomer or prodrug thereof, or a pharmaceutically acceptable salt of said compound, stereoisomer or prodrug, as defined in claim 1; and an additional compound useful to treat a condition selected from the group consisting of obesity, overweight condition, hyperlipidemia, glaucoma, cardiac arrhythmias, skin disorders, thyroid disease, hypothyroidism, thyroid cancer, diabetes, atherosclerosis, hypertension, coronary heart disease, congestive heart failure, hypercholesteremia, depression and osteoporosis.

14. A composition according to claim 13 wherein said condition is obesity.

15. A composition according to claim 13 wherein said additional compound is a lipase inhibitor.

16. A composition according to claim 15 wherein said lipase inhibitor is selected from the group consisting of lipstatin, tetrahydrolipstatin (orlistat), FL-386, WAY-121898, Bay-N-3176, valilactone, esterastin, ebelactone A, ebelactone B and RHC 80267.

17. A composition according to claim 13 wherein said additional compound is an anorectic agent.

18. A composition according to claim 16 wherein said anorectic agent is selected from the group consisting of phentermine, sibutramine, fenfluramine, dexfenfluramine and bromocriptine.

* * * * *